(12) United States Patent
Hayter et al.

(10) Patent No.: US 7,199,140 B2
(45) Date of Patent: Apr. 3, 2007

(54) VINYL PHENYL DERIVATIVES AS GLK ACTIVATORS

(75) Inventors: Barry Raymond Hayter, Cheshire (GB); Gordon Stuart Currie, Cheshire (GB); Rodney Brian Hargreaves, Cheshire (GB); Peter William Rodney Caulkett, Cheshire (GB); Roger James, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/482,264

(22) PCT Filed: Jun. 24, 2002

(86) PCT No.: PCT/GB02/02903

§ 371 (c)(1),
(2), (4) Date: Aug. 6, 2004

(87) PCT Pub. No.: WO03/000262

PCT Pub. Date: Jan. 3, 2003

(65) Prior Publication Data

US 2005/0054715 A1 Mar. 10, 2005

(30) Foreign Application Priority Data

Jun. 26, 2001 (SE) .................... 0102299

(51) Int. Cl.
*A61K 31/445* (2006.01)
*C07D 213/50* (2006.01)

(52) U.S. Cl. ............... 514/356; 546/316; 546/318

(58) Field of Classification Search ........... 546/322
See application file for complete search history.

(56) References Cited

U.S. PATENT DOCUMENTS

| 4,009,174 A | 2/1977 | Cluzan et al. | |
| 4,105,785 A | 8/1978 | Mauvernay et al. | |
| 4,146,631 A | 3/1979 | Ford et al. | |
| 4,634,783 A | 1/1987 | Fujii et al. | |
| 5,273,986 A | 12/1993 | Holland et al. | |
| 5,399,702 A | 3/1995 | Holland et al. | |
| 5,849,735 A | 12/1998 | Albright et al. | 514/220 |
| 6,110,945 A | 8/2000 | Head et al. | 514/332 |
| 6,200,995 B1 | 3/2001 | De la Brouse-Elwood et al. | 514/347 |
| 6,207,693 B1 | 3/2001 | Setoi et al. | 514/394 |
| 6,214,878 B1 * | 4/2001 | Bernardon et al. | 514/569 |
| 6,316,482 B1 | 11/2001 | Setoi et al. | 514/394 |
| 2001/0027200 A1 | 10/2001 | De la Brouse-Elwood et al. | 514/336 |

FOREIGN PATENT DOCUMENTS

| EP | 0 219 436 B1 | 12/1993 |
| EP | 0 619 116 A2 | 10/1994 |
| EP | 1048659 | 11/2000 |
| EP | 1 336 607 A1 | 8/2003 |
| EP | 1357116 | 10/2003 |
| EP | 1600442 | 11/2005 |
| FR | 2088019 | 1/1972 |
| GB | 2 216 517 A | 10/1989 |
| GB | 2 385 328 A | 8/2003 |
| JP | 57 021320 | 2/1982 |
| JP | 6-27025 | 2/1994 |
| JP | 8-143565 | 6/1996 |
| JP | 8-173525 | 7/1996 |
| JP | 08 301760 | 11/1996 |
| JP | 11 171848 | 6/1999 |
| WO | WO 95/20578 | 8/1995 |
| WO | WO-96/11902 | 4/1996 |
| WO | WO-96/22282 | 7/1996 |
| WO | WO-96/22293 | 7/1996 |
| WO | WO-96/22294 | 7/1996 |
| WO | WO-96/22295 | 7/1996 |
| WO | WO-96/41795 | 12/1996 |

(Continued)

OTHER PUBLICATIONS

DeJohn et al, "Functionalization of substituted 2(1H)- and 4(1H)-pyridones. III. The preparation of substituted 6-vinyl-1,2-dihydro-2-oxo- and 1,4-dihydro-4-oxo-3-pyridinecarboxylic acids through the chemistry of pyridone dianions," J. Heterocyclic Chem., vol. 20, pp. 1295-1302 (1983).*

(Continued)

*Primary Examiner*—Golam M. M. Shameem
*Assistant Examiner*—Andrew B. Freistein
(74) *Attorney, Agent, or Firm*—Morgan Lewis & Bockius LLP

(57) ABSTRACT

The invention relates to novel compounds of Formula (I) or a salt, solvate or prodrug thereof, wherein A, $R^1$, $R^2$, $R^3$, n and m are described in the specification, useful in the treatment of

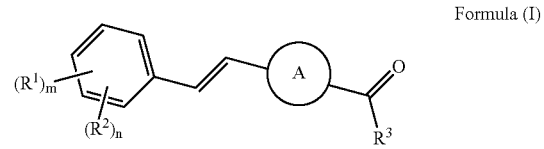

Formula (I)

a disease or condition mediated through glucokinase (GLK), such as type 2 diabetes. The invention also relates to methods for preparing compounds of Formula (I) and their use as medicaments in the treatment of diseases mediated by glucokinase.

5 Claims, No Drawings

FOREIGN PATENT DOCUMENTS

| | | |
|---|---|---|
| WO | WO-97/24355 | 7/1997 |
| WO | WO-97/49707 | 12/1997 |
| WO | WO-97/49708 | 12/1997 |
| WO | WO 98/24771 | 6/1998 |
| WO | WO 98/45242 | 10/1998 |
| WO | WO-99/00359 | 1/1999 |
| WO | WO-99/00372 | 1/1999 |
| WO | WO-99/20611 | 4/1999 |
| WO | WO-99/26944 | 6/1999 |
| WO | WO 99/38845 | 8/1999 |
| WO | WO-99/54310 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO-00/58293 | 10/2000 |
| WO | WO 01/16097 | 3/2001 |
| WO | WO-01/19788 A2 | 3/2001 |
| WO | WO-01/20327 A1 | 3/2001 |
| WO | WO-01/26652 | 4/2001 |
| WO | WO-01/44216 A1 | 6/2001 |
| WO | WO-01/83465 A2 | 11/2001 |
| WO | WO-01/83478 A2 | 11/2001 |
| WO | WO-01/85706 A1 | 11/2001 |
| WO | WO-01/85707 A1 | 11/2001 |
| WO | WO-02/08209 A1 | 1/2002 |
| WO | WO-02/14312 A1 | 2/2002 |
| WO | WO 02/24682 | 3/2002 |
| WO | WO-02/46173 A1 | 6/2002 |
| WO | WO-02/48106 A2 | 6/2002 |
| WO | WO-03/000262 A1 | 1/2003 |
| WO | WO-03/000267 A1 | 1/2003 |
| WO | WO-03/015774 A1 | 2/2003 |
| WO | WO-03/080585 A1 | 2/2003 |
| WO | WO 03/047626 | 6/2003 |
| WO | WO-03/055482 A1 | 7/2003 |
| WO | WO 03/082838 | 10/2003 |
| WO | WO-03/095438 A1 | 11/2003 |
| WO | WO-03/097824 A1 | 11/2003 |
| WO | WO-04/002481 A1 | 1/2004 |
| WO | WO-04/031179 A1 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/081001 | 9/2004 |
| WO | WO 2004/085406 | 10/2004 |
| WO | WO 2004/110375 | 12/2004 |
| WO | WO 2005/044801 | 5/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090322 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |

OTHER PUBLICATIONS

McKerrecher et al., "Discovery, Synthesis and Biological Evaluation of Novel Glucokinase Activators," Bioorganic & Medicinal Chemistry Letters 15:2103-2106 (2005).

Grimsby, "Glucokinase Activators—Potential Treatment for Type 2 Diabetes," Roche—SMI Diabetes London UK Oct. 28-29, 2002.

Levin et al., "Brain Glucose Sensing and Body Energy Homeostasis: Role in Obesity and Diabetes," American Journal of Physiology 276:R1223-R1231 (1999).

Mastafanova et al., "Synthesis and Study of the Antihypertensive Activity of Substituted N-Acetylmercaptopropionyl-6-[2'-Phenylethyl]Pipecolinic Acids," Khim Farm ZH 22(2) 294-302 (1998) (translation included).

Mastafanova et al., "Synthesis, Anti-Inflammatory and Analgesic Activity of 1,6-Disubstituted Pipecolic and 6-Substituted Picolinic Acids," Khim Farm ZH, 22(4) 428-431 (1998) (translation included).

Alvarez, E. et al., "Evidence that Glucokinase Regulatory Protein is Expressed and Interacts with Glucokinase in Rat Brain," Journal of Neurochemistry, vol. 80., pp. 45-53 (2002).

Alvarez, E. et al., "Expression of the Glucagon-Like Peptide-1 Receptor Gene in Rat Brain," Journal of Neurochemistry, vol. 66, No. 3., pp. 920-927 (1996).

Baker, R. et al. "Structure and Synthesis of Pallescensin E Utilizing a Modified Wadsworth-Emmons Reaction," J. Chem. Soc. Perkins Trans. 1, vol. 12 (1981).

Baker, R. et al. "Synthesis of Pallescensin-E: Use of Crown Ether in the Wadsworth Procedure for Olefin Formation," Tetrahedron Letters, vol. 22, Pergamon Press Ltd., GB (1981).

Bell, G.I. et al., "Glucokinase Mutations, Insulin Secretion, and Diabetes Mellitus," Annu. Rev. Physiol., vol. 58, pp. 171-186 (1996).

Beller, N.R. et al., "Photochemical Synthesis of Benzo[f]quinolines", J. Org. Chem., vol. 42, No. 22 (1997).

Brocklehurst, K.J. et al., "Stimulation of Hepatocyte Glucose Metabolism by Novel Small Molecule Glucokinase Activators," Diabetes, vol. 53, pp. 535-541 (2004).

Caro, J.F. et al., "Liver Glucokinase: Decreased Activity in Patients with Type II Diabetes," Horm. Metab. Res., vol. 27, pp. 19-22 (1995).

Christesen, H.B.T. et al., "The Second Activating Glucokinase Mutation (A456V) Implications for Glucose Homeostasis and Diabetes Therapy," Diabetes, vol. 51, pp. 1240-1246 (2002).

Corbett, W.L., "Glucokinase Activators: Discovery of Novel, Orally Active Glucose Lowering Agents," Cambridge Healthtech Institute's Eleventh Annual Molecular Medicine Tri-Conference, San Francisco, CA, Mar. 24-26, 2004.

DeFronzo, R.A., "Lilly Lecture 1987. The Triumvirate: B-Cell, Muscle, Liver. A Collusion Responsible for NIDDM," Diabetes, vol. 37, pp. 667-687 (1988).

Desai, U.J. et al., "Phenotypic Correction of Diabetic Mice by Adenovirus-Mediated Glucokinase Expression," Diabetes, vol. 50, pp. 2287-2295 (2001).

Ferre, T. et al, "Correction of Diabetic Alterations by Glucokinase," Proc. Natl. Acad. Sci. USA, vol. 93, pp. 7225-7230 (1996).

Froguel, P. et al., "Familial Hyperglycemia Due to Mutations in Glucokinase—Definition of a Subtype of Diabetes Mellitus," The New England Journal of Medicine, vol. 328, No. 10, pp. 697-702 (1993).

Fujimoto, K. et al., "Administration of D-Glucosamine into the Third Cerebroventricle Induced Feeding Accompanied by Hyperglycemia in Rats," Life Sciences, vol. 37, pp. 2475-2482 (1985).

Glaser, B. et al., "Familial Hyperinsulinism Caused by an Activating Glucokinase Mutation.".

Grimsby, J. et al., "Allosteric Activators of Glucokinase: Potential Role in Diabetes Therapy," Science, vol. 301, pp. 370-373 (2003).

Grimsby, J., "Potential Treatment for Type 2 Diabetes," Roche In-house Literature. Not Sure How to Cite.

Horsak, I. et al., "Method of Evaluation of the Phase Diagram of a System with Fromation of a Compound," Chem. Zvesti, vol. 36, No. 3 (1982).

Isomura, K. et al., "Z-type Deposition of a Polymerizable Amphiphile to Fabricate an Immobilized LB Film Showing Strong Second Harmonic Generation," Thin Solid Films, vol. 244, (1994).

Julia, M. et al., "No. 713—Synthese d'un Systeme Benzo (f) Hexahydro-2,3,4,4a,5,6 Quinoleiqui Par 'Substitution Arynique'", Bull. Chim. Soc. Fr., vol. 11 (1968).

Kamata, T. et al., "Pyroelectricity of Noncentrosymmetric Langmuir-Blodgett Films of Phenylpyrazine Derivatives," Jpn. J. Appl. Phys., vol. 33 (1994).

Knoppova, V. et al., "Synthesis and Properties of 5-Styryl-2-Furancarboxlic Acids," Collection Czechoslovak Chem. Commun., vol. 46 (1981).

Kurata, K. et al., "D-Glucose Suppression of Eating After Intr-Third Ventricle Infusion in Rat," Physiology & Behavior, vol. 37, pp. 615-620 (1986).

Kurata, K. et al., "Structural Evaluation of Glucose Analogues on Feeding Elicitation in Rat," Metabolism, vol. 38, No. 1, pp. 46-51 (1989).

Levin, B.E. et al., "Brain Glucose Sensing and Body Energy Homeostasis: Role in Obesity and Diabetes," Am. J. Physiol. Endocrinol. Metab Incomplete Ref-Check April Letter.

Levin, B.E. et al., "Differential Effects of Diet and Obesity on High and Low Affinity Sulfonylurea Binding Sites in the Rat Brain," Brain Research, vol. 739, pp. 293-300 (1996).

Levin, B.E. et al., "Reduced Glucose-induced Neuronal Activation in the Hypothalamus of Diet-induced Obese Rats," Brain Research, vol. 808, p. 317-319 (1998).

Levin, B.E., "Glucosensing Neurons Do More than Just Sense Glucose," International Journal of Obesity, vol. 26, Suppl. 5, pp. 568-572 (2001).

Levin, B.E., "In Vivo and In Vitro Regulation of [3H]Glyburide Binding to Brain Sulfonylurea Receptors in Obesity-Prone and Resistant Rats by Glucose," Brain Research, vol. 776, pp. 146-153 (1997).

Lynch, R.M. et al., "Localization of Glucokinase Gene Expression in the Rat Brain," Diabetes, vol. 49, pp. 693-700 (2000).

Mobbs, C.V. et al., "Brain Glucose-sensing Mechanisms: Ubiquitous Silencing by Aglycemia vs. Hypothalamic Neuroendocrine Responses," Am. J. Phsyiol. Endocrinol. Metab., vol. 281, pp. E649-E654 (2001).

Moore, M.C. et al., "Acute Fructose Administration Improves Oral Glucose Tolerance in Adults with Type 2 Diabetes," Diabetes Care, vol. 24, No. 11, pp. 1882-1887 (2001).

Printz, R.L. et al., "Mammalian Glucokinase," Annu. Rev. Nur., vol. 13, pp. 463-496 (1993).

Prousek, J. et al., "Preparation and Electron Transfer-Induced cis-trans Isomerization Reactions of 1-(5-Nitro-2-Furyl)-, 1-(5-Nitro-2-Thienyl)-, and 1-(4-Nitrophenyl)-2-R Ethylenes," Collect. Czech. Chem. Commun., vol. 54 (1989).

Qian-Cutrone, J. et al., "Glucolipsin A and B, Two New Glucokinase Activators Produced by Streptomyces Purpurogenisclroticus and Nocardia Vaccinii," The Journal of Antibiotics, vol. 52, No. 3, pp. 245-255 (1999).

Roncero, I. et al., "Functional Glucokinase Isoforms Are Expressed in Rat Brain," Journal of Neurochemistry, vol. 74, No. 5 (2000).

Rowe, I.C.M. et al. "Potassium Channel Dysfunction in Hypothalamic Glucose-receptive Neurones of Obese Zucker Rats," Journal of Physiology, vol. 497.2, pp. 365-377 (1996).

Schuit, F.C. et al., "Glucose Sensing in Pancreatic B-Cells: A Model for the Study of Other Glucose-Regulated Cells in Gut, Pancreas, and Hypothalamus," Diabetes, vol. 50, pp. 1-11 (2001).

Seoane, J. et al., "Glucokinase Overexpression Restores Glucose Utilization and Storage in Cultured Hepatocytes from Male Zucker Diabetic Fatty Rats," The Journal of Biological Chemistry, vol. 274, No. 45, pp. 31833-31838 (1999).

Shepard, K.L., et al., "Imino-Bridged Heterocycles. VII. (1) N-Aminobenzocycloheptapyridinimines," J. Heterocyclic Chem., vol. 23 (1986).

Shiota, M. et al., Glucokinase Gene Locus Transgenic Mice are Resistant to the Development of Obesity-Induced Type 2 Diabetes, Diabetes, vol. 50, pp. 622-629 (2001).

Spanswick, D. et al., "Insulin Activates ATP-Sensitive K+ Channels in Hypothalamic Neurons of Lean, but not Obese Rats," Neuroscience, vol. 3, No. 8, pp. 757-758 (2000).

Spanswick, D. et al., "Leptin Inhibits Hypothalamic Neurons by Activation of ATP-Sensitive Potassium Channels," Nature, vol. 390, pp. 521-525 (1997).

Tucker, H. et al., "Novel Inhibitors of Prolyl 4-Hydroxylase. 2. 5-Amide Substituted Pyridine-2-Carboxylic Acids," J. Med. Chem., vol. 35 (1992).

vanderStelt, C. et al., "Synthesis and Pharmacological Properties of Some Derivatives of 5H-Benzo [4,5] Cyclohepta [1,2-b] Pyridine and of 11H-Benzo [5,6] Cyclohepta [1,2-c] Pyridine III," Arzneim.-Forsch., vol. 22, No. 1 (1972).

Velho, G. et al., "Impaired Hepatic Glycogen Synthesis in Glucokinase-Deficient (MODY-2) Subjects," J. Clin. Invest., vol. 98, no. 8, pp. 1755-1761 (1996).

Yakushijin, K. et al., "Intramolecular Ring Formation of Phenyl Azide and Furan Moieties," Chem. Pharm. Bull., vol. 30, No. 1 (1982).

Yakushijin, K. et al., "Intramolecular Ring Formation of Phenyl Azide and Furan," Heterocycles, vol. 12, No. 8 (1979).

Yang, X-J. et al., "Hypothalamic Glucose Sensor," Similarities to and Differences From Pancreatic B-Cell Mechanisms, Diabetes, vol. 48, pp. 1763-1772 (1999).

Yoshina, S. et al., "Studies of Heterocyclic Compounds. II. Synthesis of 2-Furylvinyl-benzenes and Studies of Polarography," Yakugaku Zasshi, vol. 88, No. 4, pp. 398-404 (1968).

Yoshina, S. et al., "Studies of Heterocyclic Compounds. IV. Ultraviolet Spectra of 2-(2-Furyl)vinylbenzenes and 2-(2-Furyl) vinylfurans," Yakugaku Zasshi, vol. 88, No. 4, pp. 410-416, (1968).

Yoshina, S. et al., "Studies of Heterocyclic Compounds. VI. 2-(Carbomethoxy-2-furyl)vinyl Benzenes and Their Ultraviolet Spectra," Yakugaku Zasshi, vol. 88, No. 4, pp. 977-983, (1968).

Yoshina, S. et al., "Studies of Heterocyclin Compounds. III. Shythesis of Methyl 5-(2-Phenylvinyl)-2-Furoate," Yakugaku Zasshi 88(4):405-409 (1968).

Youssefyeh, R.D. et al., "Development of High-Affinity 5-HT3 Receptor Antagonists. 1. Initial Structure-Activity Relationship of Novel Benzamides," J. Med. Chem., vol. 35 (1992).

Bonina, F. et al., "Sintesi e Attivita Farmacologica di Acidi 2-Arileteniltiazol-4-acetici e 4-Carbossilici," Farmaco Ed. Sci., vol. 40. No. 11, pp. 875-884 (1985).

Ciaceri, G., et al., "Azione Analgesica, Antipiretica E Antiflogistica di Alcuni Nuovi Acidi Della Serie Feniletilentiazolica," Minerva Medica (1972).

Plieninger et al., "Synthese der 7.8-Dihydro-5.6-Benzochinolin-Carbonsaure-(3)," Chem. Ber. 87:882-887 (1954).

Rivalle, C. et al., "Furannes et Pyrroles Disubstitutes en 2,3-XVIII: Synthese et Rearrangement de 4H-Dihydro-9,10 Benzo[4,5] Cyclohepta [1,2-b] Furannones-4," Tetrahedron, vol. 32, Pergamon Press (1976).

Carroll et al. "The in vitro characterisation of a novel Glucokinase activator" Stress, Signalling and Control, Biochemical Society Meeting 679, University of Essex, UK (Jul. 2-4, 2003).

Coghlan "Small molecule Glucokinase Activators (GKAs) as novel anti-diabetic agents" Society for Medicines Research Seminar (Jun. 2004).

Coghlan "Small molecule Glucokinase Activators (GKAs) as novel anti-diabetic agents" CIDEM seminar (May 2005).

Edmont et al. "Synthesis and evaluation of quinoline carboxyguanidines as antidiabetic agents" Bioorg Med Chem Lett. 10(16):1831-1834 (2000).

Ford et al. "Synthesis and quantitative structure-activity relationships of antiallergic 2-hydroxy-N-1H-tetrazol-5-ylbenzmides and N-(2-hydroxyphenyl)-1H-tetrazole-5-carboxamides" J Med Chem. 29(4):538-549 (1986).

Gill et al. "Stimulation of insulin release by a small molecule glucokinase activator" EASD Islet Study Group Abstract (Nov. 2005).

Julia et al. Synthesis of a 2,3,4,4a,5,6-hexahydrobenzo[f]quinoline system by "aryne substitution" Bull Chem Soc France, vol. 11, 4463-4467 (1968) (Translation enclosed).

Kar A. "Cinchophen analogues as potential CNS agents" J Pharm Sci. 72(9):1082-1084 (Sep. 1983).

Leighton et al. "Small molecule glucokinase activators as novel anti-diabetic agents" Biochem Soc Trans. 33(Pt 2):371-374 (Apr. 2005).

Mastafanova et al. "Features of the catalytic reduction of 4-(3-oxoquinuclidyl-2-methylene)-6-methoxyquinoline and its ethyleneketal" kim Geterotsiki Soedin (1):86-94 (1989) (Translation enclosed).

McKerrecher "Design and synthesis of novel glucokinase activators" 13th RSC-SCI Medicinal Chemistry Symposium, Churchill College Cambridge (Sep. 2005).

McKerrecher et al. "Design and synthesis of novel glucokinase activators as potential treatment for type 2 diabetes" Frontiers in Medicinal Chemistry, Frankfurt (Mar. 2006).

McKerrecher et al. "Design of a potent, soluble glucokinase activator with excellent in vivo efficacy" Bioorg Med Chem Lett. 16(10):2705-2709 (May 15, 2006) Epub Feb. 28, 2006.

McKerrecher et al. "Identification of orally bioavailable small molecule activators of gluckinase" Abstract, Anglo-Swedish Medicinal Chemistry Meeting (Mar. 2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, Anaheim, California, Mar. 28-Apr. 1, 2004 (paper 341).

Tornetta et al. "Arylvinylthiazole derivatives with anti-inflammatory, analgesic and anti-pyretic activity" Boll Sedute Accad Giovenia Sci Nat Catanic 11(9-10):89-95 (1973) (Translation enclosed).

Vertigan et al. "Impact of cell glycogen content on modulation of hepatocyte glucose metabolism by pharmacological agents" Diabetologia, vol. 47 Supp 1, A214, 589 (2004).

Williams et al. "Meeting the Needs of Type 2 Diabetes Patients" Highlights from the Society for Medicines Research symposium Type 2 Diabetes: Mechanisms and Emerging Therapeutic Targets, held Jun. 17, 2004, in London, United Kingdom, Drug News and Perspectives 17(8) 1-4 (Oct. 2004).

Zhang et al. "Synthesis based on affinity separation (SAS): separation of products having barbituric acid tag from untagged compounds using hydrogen bond interaction" Synlett 5:590-596 (2001).

Belstein Registry No. 6511458 (Apr. 18, 1994), [XP002272206].

Chemical Abstracts Service, Columbus, Ohio, US: CAS Registry No. 438028-05-8 (Nov. 15, 2001); CAS Registry No. 438024-90-9 (Nov. 15, 2001), [XP002272448].

Chemical Abstracts Service, Columbus, Ohio, US: CAS Registry No. 445284-93-5 (Jul. 9, 2002); CAS Registry No. 445250-52-2 (Jul. 2, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry NO. 353474-36-9 (Jul. 9, 2002); CAS Registry No. 362473-72-1 (Jul. 9, 2002); CAS Registry No. 303140-37-6 (Jul. 9, 2002); [XP002272449].

* cited by examiner

VINYL PHENYL DERIVATIVES AS GLK ACTIVATORS

CROSS-REFERENCE TO RELATED APPLICATIONS

This application is a national stage filing under 35 U.S.C. 371 of International Application No. PCT/GB02/02903, filed Jun. 24, 2002, which claims priority from Sweden Patent Application No. 0102299-5, filed Jun. 26, 2001 the specifications of which are incorporated by reference herein. International Application No. PCT/GB02/02903 was published under PCT Article 21 (2) in English.

FIELD OF THE INVENTION

The present invention relates to compounds which activate glucokinase (GLK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising a compound of the invention, and use of such a compound in the conditions described above.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6–10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Type 2 maturity-onset diabetes of the young (MODY-2), the diabetes is caused by GLK loss of function mutations [3, 4]. Hyperglycaemia in MODY-2 patients results from defective glucose utilisation in both the pancreas and liver [5]. Defective glucose utilisation in the pancreas of MODY-2 patients results in a raised threshold for glucose stimulated insulin secretion. Conversely, rare activating mutations of GLK reduce this threshold resulting in familial hyperinsulinism [6, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9–12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is elevated in the post-absorptive state whereas F1P predominates in the post-prandial state. In contrast to the hepatocyte, the pancreatic β-cell expresses GLK in the absence of GLKRP. Therefore, β- cell GLK activity is regulated exclusively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act exclusively in the liver. However, compounds with either profile are predicted to be of therapeutic benefit in treating Type 2 diabetes as this disease is characterised by defective glucose utilisation in both tissues.

In WO0058293 and WO 01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described in Example A.

In WO9622282/93/94/95 and WO9749707/8 are disclosed a number of intermediates used in the preparation of compounds useful as vasopressin agents which are related to those disclosed in the present invention. Related compounds are also disclosed in WO9641795 and JP8143565 (vasopressin antagonism), in JP8301760 (skin damage prevention) and in EP619116 (osetopathy).

We present as a feature of the invention the use of a compound of Formula (I) or a salt, pro-drug or solvate thereof, in the preparation of a medicament for use in the treatment or prevention of a disease or medical condition mediated through GLK:

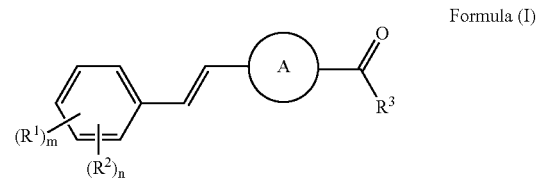

Formula (I)

wherein
  A is heteroaryl;
  m is 0, 1, or 2;
  n is 0, 1, 2, 3 or 4;
  and n+m>0;
  each $R^1$ is independently selected from OH, —$(CH_2)_{1-4}$OH, —$CH_{3-a}F_a$, —$(CH_2)_{1-4}CH_{3-a}F_a$, —$OCH_{3-a}F_a$, halo, $C_{1-6}$alkyl, $C_{2-6}$alkenyl, $C_{2-6}$alkynyl, $NO_2$, $NH_2$, —NH-$C_{1-4}$alkyl, —N—di—($C_{1-4}$alkyl), CN, formyl, phenyl or heterocyclyl optionally substituted by $C_{1-6}$alkyl;
  each $R^2$ is the group Y—X—
    wherein each X is a linker independently selected from:
      —Z—, —O—Z—, —O—Z—O—Z—, —C(O)O—Z—, —OC(O)—Z—, —S—Z—, —SO—Z—, —$SO_2$—Z—, —N($R^7$)—Z—, —N($R^7$)$SO_2$—Z—, —$SO_2$N($R^7$)—Z—, —$(CH_2)_{1-4}$—, —CH=CH—Z—, —C≡C—Z—, —N($R^7$)

CO—Z—, —CON(R$^7$)—Z—, —C(O)N(R$^7$)S(O)$_2$—Z—, —S(O)$_2$N(R$^7$)C(O)—Z—, —C(O)—Z— or a direct bond;

each Z is independently a direct bond, C$_{2-6}$alkenylene or a group of the formula —(CH$_2$)$_p$—C(R$^7$)$_2$—(CH$_2$)$_q$—;

each Y is independently selected from aryl-Z$^1$—, heterocyclyl-Z$^1$—, C$_{3-7}$cycloalkyl-Z$^1$—, C$_{1-6}$alkyl, C$_{2-6}$alkenyl, C$_{2-6}$alkynyl, —(CH$_2$)$_{1-4}$CH$_{3-a}$F$_a$ or —CH(OH)CH$_{3-a}$F$_a$; wherein each Y is independently optionally substituted by up to 3 R$^4$ groups;

each R$^4$ is independently selected from halo, —CH$_{3-a}$F$_a$, CN, NO$_2$, NH$_2$, C$_{1-6}$alkyl, —OC$_{1-6}$alkyl, —COOH, —C(O)OC$_{1-6}$alkyl, OH or phenyl optionally substituted by C$_{1-6}$alkyl or —C(O)OC$_{1-6}$alkyl, or R$^5$—X$^1$—, where X$^1$ is independently as defined in X above and R$^5$ is selected from hydrogen, C$_{1-6}$alkyl, —CH$_{3-a}$F$_a$; phenyl, naphthyl, heterocyclyl or C$_{3-7}$cycloalkyl; and R$^5$ is optionally substituted by halo, C$_{1-6}$alkyl, —CH$_{3-a}$F$_a$; CN, NO$_2$, NH$_2$, COOH, or —C(O)OC$_{1-6}$alkyl, wherein each phenyl, naphthyl or heterocyclyl ring in R$^5$ is optionally substituted by halo, CH$_{3-a}$F$_a$, CN, NO$_2$, NH$_2$, C$_{1-6}$alkyl, —OC$_{1-6}$alkyl, COOH, —C(O)OC$_{1-6}$alkyl or OH;

each Z$^1$ is independently a direct bond, C$_{2-6}$alkenylene or a group of the formula —(CH$_2$)$_p$—C(R$^6$)$_2$—(CH$_2$)$_q$—;

R$^3$ is selected from OH, —O-C$_{1-6}$alkyl or NHR$^6$;

R$^6$ is selected from hydrogen, C$_{1-6}$alkyl, —O-C$_{1-6}$alkyl, —SO$_2$C$_{1-6}$alkyl, —(CH$_2$)$_{0-3}$OH;

R$^7$ is independently selected from hydrogen, C$_{1-6}$alkyl or —C$_{2-4}$alkyl-O-C$_{1-4}$alkyl;

each a is independently 1, 2 or 3;

p is an integer between 0 and 2;

q is an integer between 0 and 2;

and p+q<4.

According to a further feature of the invention there is provided the use of a compound of Formula (Ia) or a salt, pro-drug or solvate thereof, in the preparation of a medicament for use n the treatment or prevention of a disease or medical condition mediated through GLK:

Formula (Ia)

wherein m is 0, 1 or 2;

n is 0, 1, 2, 3 or 4;

and n+m>0;

each R$^1$ is independently selected from OH, (CH$_2$)$_{1-4}$OH, CH$_{3-a}$F$_a$, (CH$_2$)$_{1-4}$CH$_{3-a}$F$_a$, OCH$_{3-a}$F$_a$, halo, C$_{1-6}$ alkyl, C$_{2-6}$alkenyl, C$_{2-6}$alkynyl, NO$_2$, NH$_2$, CN, phenyl or a heterocyclyl optionally substituted by C$_{1-6}$alkyl;

each R$^2$ is the group Y—X— wherein each X is a linker independently selected from —O(CH$_2$)$_{0-3}$—, —(CH$_2$)$_{0-3}$O—, —C(O)O(CH$_2$)$_{0-3}$—, —S(CH$_2$)$_{0-3}$—, —SO(CH$_2$)$_{0-3}$—, —SO$_2$(CH$_2$)$_{0-3}$—, —NHSO$_2$—, —SO$_2$NH—, —(CH$_2$)$_{1-4}$—, —CH=CH(CH$_2$)$_{0-2}$—, —C≡C(CH$_2$)$_{0-2}$—, —NHCO—, —CONH—;

each Y is independently selected from phenyl(CH$_2$)$_{0-2}$, naphthyl(CH$_2$)$_{0-2}$, heterocyclyl(CH$_2$)$_{0-2}$, C$_{3-7}$cycloalkyl(CH$_2$)$_{0-2}$, C$_{1-6}$ alkyl, OC$_{1-6}$alkyl, C$_{2-6}$ alkenyl, C$_{2-6}$ alkynyl, or CH(OH)CH$_{3-a}$F$_a$; wherein each Y is independently optionally substituted by one or more R$^4$ groups;

each R$^4$ is independently selected from halo, CH$_{3-a}$F$_a$, OCH$_{3-a}$F$_a$, CN, NO$_2$, NH$_2$, C$_{1-6}$alkyl, OC$_{1-6}$ alkyl, COOH, (CH$_2$)$_{0-3}$COOH, O(CH$_2$)$_{0-3}$COOH, C(O)OC$_{1-6}$alkyl, C$_{1-6}$alkyl, C$_{1-6}$alkyl(O)OC$_{1-6}$ alkyl, CO-phenyl, CONH$_2$, CONH-phenyl, SO$_2$NH$_2$, SO$_2$C$_{1-6}$alkyl, OH, or phenyl optionally substituted by one or more R$^5$ groups where R$^5$ is selected from hydrogen, C$_{1-6}$alkyl or C(O)OC$_{1-6}$alkyl.

each a is independently 1, 2 or 3;

R$^3$ is selected from hydrogen, C$_{1-6}$alkyl or NHR$^6$;

R$^6$ is selected from hydrogen, C$_{1-6}$alkyl, OC$_{1-6}$alkyl, SO$_2$C$_{1-6}$alkyl, (CH$_2$)$_{0-3}$OH.

According to a further feature of the invention there is provide a compound of Formula (Ib) or a salt, solvate or pro-drug thereof;

Formula (Ib)

wherein

A is heteroaryl;

m is 0, 1 or 2;

n is 0, 1, 2, 3 or 4;

and n+m>0;

each R$^1$ is independently selected from OH, —(CH$_2$)$_{1-4}$OH, —CH$_{3-a}$F$_a$, —(CH$_2$)$_{1-4}$CH$_{3-a}$F$_a$, —OCH$_{3-a}$F$_a$, halo, C$_{1-6}$alkyl, C$_{2-6}$alkenyl, C$_{2-6}$alkynyl, NO$_2$, NH$_2$, —NH-C$_{1-4}$alkyl, —N-di-(C$_{1-4}$alkyl), CN, formyl, phenyl or heterocyclyl optionally substituted by C$_{1-6}$alkyl;

each R$^2$ is the group Y—X— wherein each X is a linker independently selected from:
—Z—, —O—Z—, —O—Z—O—Z—, —C(O)O—Z—, —OC(O)—Z—, —S—Z—, —SO—Z—, —SO$_2$—Z—, —N(R$^7$)—Z—, —N(R$^7$)SO$_2$—Z—, —SO$_2$N(R$^7$)—Z—, —(CH$_2$)$_{1-4}$—, —CH=CH—Z—, —C≡C—Z—, —N(R$^7$)CO—Z—, —CON(R$^7$)—Z—, —C(O)N(R$^7$)S(O)$_2$—Z—, —S(O)$_2$N(R$^7$)C(O)—Z—, —C(O)—Z— or a direct bond;

each Z is independently a direct bond, C$_{2-6}$alkenylene or a group of the formula —(CH$_2$)$_p$—C(R$^7$)$_2$—(CH$_2$)$_q$—;

each Y is independently selected from aryl-Z$^1$—, heterocyclyl-Z$^1$—, C$_{3-7}$cycloalkyl-Z$^1$—, C$_{1-6}$alkyl, C$_{2-6}$alkenyl, C$_{2-6}$alkynyl, —(CH$_2$)$_{1-4}$CH$_{3-a}$F$_a$ or —CH(OH)CH$_{3-a}$F$_a$; wherein each Y is independently optionally substituted by up to 3 R$^4$ groups;

each R$^4$ is independently selected from halo, —CH$_{3-a}$F$_a$, CN, NO$_2$, NH$_2$, C$_{1-6}$alkyl, —OC$_{1-6}$alkyl, —COOH, —C(O)OC$_{1-6}$alkyl, OH or phenyl optionally substituted by C$_{1-6}$alkyl or —C(O)OC$_{1-6}$alkyl, or R$^5$—X$^1$—, where X$^1$ is independently as defined in X above and R$^5$ is selected from hydrogen, $C_{1-6}$alkyl, —$CH_{3-a}F_a$, phenyl, naphthyl, heterocyclyl or $C_{3-7}$cycloalkyl; and $R^5$ is optionally substituted by halo, $C_{1-6}$alkyl, —$CH_{3-a}F_a$, CN, $NO_2$, $NH_2$, COOH, or —C(O)O$C_{1-6}$alkyl,
  wherein each phenyl, naphthyl or heterocyclyl ring in $R^5$ is optionally substituted by halo, $CH_{3-a}F_a$, CN, $NO_2$, $NH_2$, $C_{1-6}$alkyl, —O$C_{1-6}$alkyl, COOH, —C(O)O$C_{1-6}$alkyl or OH;

each $Z^1$ is independently a direct bond, $C_{2-6}$alkenylene or a group of the formula —$(CH_2)_p$—$C(R^6)_2$—$(CH_2)_q$—;
$R^3$ is selected from OH, —O-$C_{1-6}$alkyl or $NHR^6$;
$R^6$ is selected from hydrogen, $C_{1-6}$alkyl, —O—$C_{1-6}$alkyl, —$SO_2C_{1-6}$alkyl, —$(CH_2)_{0-3}$OH;
$R^7$ is independently selected from hydrogen, $C_{1-6}$alkyl or —$C_{2-4}$alkyl-O-$C_{1-4}$alkyl;
each a is independently 1, 2 or 3;
p is an integer between 0 and 2;
q is an integer between 0 and 2;
and p+q<4;
with the proviso that:
(i) where m is 1 or 2 and n is 0, $R^3$ is OH or —O-$C_{1-6}$alkyl, then $R^1$ is other than OH, CN, halo, methyl, amino or nitro;
(ii) when m=0, n=1, X is —O—, —O—C(O)—, —S—, —S(O)—, —S($O_2$)—, —N($CH_3$)—, —N($CH_3$)—$CH_2$— or —C(O)—NH—, $R^3$ is OH or —O-$C_{1-6}$alkyl, then Y cannot be $C_{1-6}$alkyl or $C_{1-6}$alkyl substituted by $C_{1-6}$alkyl;
(iii) when m is 0 or m is 1 and $R^1$ is $NO_2$, $R^3$ is OH or —O-$C_{1-6}$alkyl, then when n is 2 $(R^2)_n$ cannot be di-$C_{1-6}$alkyl-O— or $C_{1-6}$alkyl-O— $C_{1-6}$alkenyl-O— and when n is 3 $(R^2)_n$ cannot be tri-$C_{1-6}$alkyl-O—;
(iv) when A is pyridyl, m is 0 or m is 1 and $R^1$ is halo, n is 1 and $R^2$ is phenyl, phenyl-$CH_2$—O— or pyridyl-NH—, then $R^3$ cannot be OH or —O-$C_{1-6}$alkyl; and
(v) when A is pyridyl, $R^3$ is OH, m is 0, n is 2 and one of the $R^2$ groups is phenyl-$CH_2$—O—, then the other $R^2$ group must be other than $CH_3$—S— or $CH_3$—$SO_2$—.

According to a further feature of the invention there is provided a compound of Formula (Ib) or salt, solvate of pro-drug thereof,
wherein A is pyridyl
with the proviso that
(i) when m is 1 or 2 and n is 0 then $R^1$ is other than halo, methyl, amino or nitro;
(ii) when m=0, n=1, X is —O—, —S—, —S(O)—, —S($O_2$)—, —N($CH_3$)—, or —N($CH_3$)—$CH_2$—, $R^3$ is OH or —O-$C_{1-6}$alkyl, then Y cannot be methyl;
(iii) when $R^3$ is OH, m is 0, n is 2 and one of the $R^2$ groups is phenyl —$CH_2$—O—, then the other $R^2$ group must be other than $CH_3$—S— or $CH_3$—$SO_2$—; and
(iv) when m is 0 or m is 1 and $R^1$ is halo, n is 1 and $R^2$ is phenyl, phenyl-$CH_2$—O— or pyridyl-NH—, then $R^3$ cannot be OH or —O-$C_{1-6}$alkyl;

According to a further feature of the invention there is provided a compound of Formula (Ic) or a salt, solvate or pro-drug thereof;

Formula (Ic)

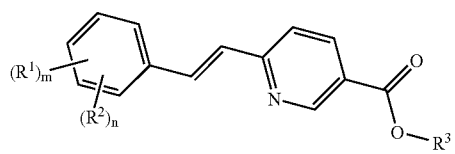

wherein
m is 0, 1 or 2;
n is 0, 1, 2, 3 or 4;
and n+m>0;
each $R^1$ is independently selected from OH, $(CH_2)_{1-4}$OH, $CH_{3-a}F_a$, $(CH_2)_{1-4}CH_{3-a}F_a$, $OCH_{3-a}F_a$, halo, $C_{1-6}$alkyl, $C_{2-6}$alkenyl, $C_{2-6}$alkynyl, $NO_2$, CN, phenyl or a heterocyclyl optionally substituted by $C_{1-6}$alkyl;
each $R^2$ is the group Y—X—
  wherein each X is a linker independently selected from —O$(CH_2)_{0-3}$—, —$(CH_2)_{0-3}$O—, —C(O)O$(CH_2)_{0-3}$—, —S$(CH_2)_{0-3}$—, —SO$(CH_2)_{0-3}$—, —$SO_2$ $(CH_2)_{0-3}$—, —$NHSO_2$—, —$SO_2$NH—, —$(CH_2)_{1-4}$—, —CH=CH$(CH_2)_{0-2}$—, —C≡C$(CH_2)_{0-2}$—, —NHCO—, —CONH—;
  each Y is independently selected from phenyl$(CH_2)_{0-2}$, naphthyl $(CH_2)_{0-2}$, heterocyclyl$(CH_2)_{0-2}$, $C_{3-7}$ cycloalkyl $(CH_2)_{0-2}$, $C_{1-6}$ alkyl, O$C_{1-6}$alkyl, $C_{2-6}$ alkenyl, $C_{2-6}$ alkynyl, or CH(OH)$CH_{3-a}F_a$; where each Y is independently optionally substituted by one or more $R^4$ groups;
  each $R^4$ is independently selected from halo, $CH_{3-a}F_a$, $OCH_{3-a}F_a$, CN, $NO_2$, $NH_2$, $C_{1-6}$alkyl, $OC_{1-6}$alkyl, COOH, $(CH_2)_{0-3}$COOH, O$(CH_2)_{0-3}$COOH, C(O)O$C_{1-6}$alkyl, $C_{1-6}$alkyl(O)O$C_{1-6}$alkyl, CO-phenyl, $CONH_2$, CONH-phenyl, $SO_2NH_2$, $SO_2C_{1-6}$alkyl, OH, or phenyl optionally substituted by one or more $R^5$ groups where $R^5$ is selected from hydrogen, $C_{1-6}$alkyl or C(O)O$C_{1-6}$alkyl.

each a is independently 1, 2 or 3;
$R^3$ is selected from hydrogen, $C_{1-6}$alkyl or $NHR^6$;
$R^6$ is selected from hydrogen, $C_{1-6}$alkyl, O$C_{1-6}$alkyl, $SO_2C_{1-6}$alkyl, $(CH_2)_{0-3}$OH;
with the proviso that:
(i) when $R^3$ is H, m is 0, n is 2 and one of the $R^2$ groups is phenyl-$CH_2$—O—, then the other $R^2$ group must be other than $CH_3$—S— or $CH_3$—$SO_2$—; and
(ii) when $R^3$ is H, m is 1, n is 1 and $R^2$ is phenyl-$CH_2$—O—, then $R^1$ must be other than halo.

Compounds of the invention may form salts which are within the ambit of the invention. Pharmaceutically acceptable salts are preferred although other salts may be useful in, for example, isolating or purifying compounds.

The term "aryl" refers to phenyl, naphthyl or a partially saturated bicyclic carbocyclic ring containing between 8 and 12 carbon atoms, preferably between 8 and 10 carbon atoms. Example of partially saturated bicyclic carbocyclic ring include: 1,2,3,4-tetrahydronaphthyl, indanyl, indenyl, 1,2, 4a,5,8,8a-hexahydronaphthyyl or 1,3a-dihydropentalene.

The term "halo" includes fluoro, chloro, bromo and iodo; preferably chloro, bromo and fluoro; most preferably fluoro.

The expression "—$CH_{3-a}F_a$" wherein a is an integer between 1 and 3 refers to a methyl group in which 1, 2 or all 3 hydrogen are replaced by a fluorine atom. Examples include: trifluoromethyl, difluoromethyl and fluoromethylene An analogous notation is used with reference to the group —$(CH_2)_{1-4}CH_{3-a}F_a$, examples include: 2,2-difluoroethyl and 3,3,3-trifluoropropyl.

In this specification the term "alkyl" includes both straight and branched chain alkyl groups. For example, "$C_{1-4}$alkyl" includes propyl, isopropyl and tert-butyl.

The term "heteroaryl" refers to a monocyclic aromatic heterocyclic ring containing between 5–6 atoms of which at least one atom is chosen from nitrogen, sulphur or oxygen, which may, unless otherwise specified, be carbon or nitrogen linked, wherein a —$CH_2$— group can optionally be replaced by a —C(O)— and sulphur atoms in a heterocyclic ring may be oxidised to S(O) or S(O)$_2$ groups. Examples of "heteroaryl" include: thiazolidinyl, pyrrolidinyl, pyrrolinyl, 2-oxopyrrolidinyl, 2,5-dioxopyrrolidinyl, 1,1-dioxotetrahydrothienyl, 2,4-dioxoimidazolidinyl, 2-oxo-1,3,4-(4-triazolinyl), 2-oxo-oxazolidininyl, 5,6-dihydrouracilyl, 1,2,4-oxadiazolyl, 4-oxothiazolidinyl, morpholinyl, furanyl, 2-oxotetrahydrofuranyl, tetrahydrofuranyl, thienyl, isoxazolyl, tetrahydropyranyl, piperidyl, piperazinyl, thiomorpholinyl, 1,1-dioxothiomorpholinyl, tetrahydropyranyl, 1,3-dioxolanyl, homopiperazinyl, isoxazolyl, imidazolyl, pyrrolyl, thiazolyl, thiadiazolyl, isothiazolyl, 1,2,4-triazolyl, 1,2,3-triazolyl, pyranyl, pyrimidyl, pyrazinyl, pyridazinyl, pyridyl, 4-oxo-pyridinyl, 1,1-dioxotetrahydrothienyl. Preferably "heteroaryl" is selected from: pyridyl, pyrimidinyl, pyrazinyl, furanyl or thiazolyl.

The term "heterocyclyl" is a saturated, partially saturated or unsaturated, mono or bicyclic ring containing 3–12 atoms of which at least one atom is chosen from nitrogen, sulphur or oxygen, which may, unless otherwise specified, be carbon or nitrogen linked, wherein a —CH$_2$— group can optionally be replaced by a —C(O)— and sulphur atoms in a heterocyclic ring may be oxidised to S(O) or S(O)$_2$ groups. Preferably a "heterocyclyl" is a saturated, partially saturated or unsaturated, mono or bicyclic ring (preferably monocyclic) containing 5 or 6 atoms of which 1 to 3 atoms are nitrogen, sulphur or oxygen, which may, unless otherwise specified, be carbon or nitrogen linked, wherein a —CH$_2$— group can optionally be replaced by a —C(O)— or sulphur atoms in a heterocyclic ring may be oxidised to S(O) or S(O)$_2$ groups. Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, furanyl, 2-oxotetrahydrofuranyl, tetrahydrofuranyl, 2,3-dihydrobenzofuranyl, benzothienyl, isoxazolyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiazolyl, thiadiazolyl, isothiazolyl, 1,2,4-triazolyl, 1,2,3-triazolyl, pyranyl, indolyl, pyrimidyl, pyrazinyl, pyridazinyl, pyridyl, 4-pyridonyl, quinolyl, tetrahydrothienyl 1,1-dioxide, 2-oxo-pyrrolidinyl and 1-isoquinolonyl. Preferred examples of "heterocyclyl" when referring to a 5/6 and 6/6 bicyclic ring system include benzofuranyl, benzimidazolyl, benzthiophenyl, benzthiazolyl, benzisothiazolyl, benzoxazolyl, benzisoxazolyl, pyridoimidazolyl, pyrimidoimidazolyl, quinolinyl, isoquinolinyl, quinoxalinyl, quinazolinyl, phthalazinyl, cinnolinyl, imidazo[2,1-b][1,3]thiazolyl, chromanyl and naphthyridinyl. Preferably the term "heterocyclyl" refers to 5- or 6-membered monocyclic heterocyclic rings, such as oxazolyl, isoxazolyl, pyrrolidinyl, 2-pyrrolidonyl, 2,5-dioxopyrrolidinyl, morpholino, furanyl, tetrahydrofuranyl, piperidyl, piperazinyl, thiomorpholino, tetrahydropyranyl, homopiperazinyl, thienyl, imidazolyl, 1,24-triazolyl, 1,3,4-triazolyl, indolyl, thiazolyl, thiadiazolyl, pyrazinyl, pyridazinyl and pyridyl.

The term "cycloalkyl" refers to a saturated carbocyclic ring containing between 3 to 12 carbon atoms, preferably between 3 and 7 carbon atoms. Examples of $C_{3-7}$cycloalkyl include cycloheptyl, cyclohexyl, cyclopentyl, cyclobutyl or cyclopropyl. Preferably cyclopropyl, cyclopentyl or cyclohexyl.

Examples of $C_{1-6}$alkyl include methyl, ethyl, propyl, isopropyl, 1-methyl-propyl, sec-butyl, tert-butyl and 2-ethyl-butyl; examples of $C_{2-6}$alkenyl include: ethenyl, 2-propenyl, 2-butenyl, or 2-methyl-2-butenyl; examples of $C_{2-6}$alkynyl include: ethynyl, 2-propynyl, 2-butynyl, or 2-methyl-2-butynyl, examples of —OC$_{1-6}$alkyl include methoxy, ethoky, propoxy and tert-butoxy; examples of —C(O)OC$_{1-6}$alkyl include methoxycarbonyl, ethoxycarbonyl and tert-butyloxycarbonyl; examples of —NH—C$_{1-4}$alkyl include:

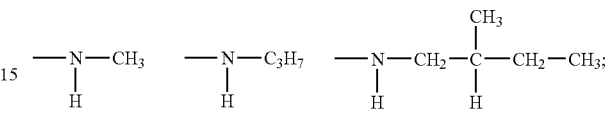

and examples of —N—di-($C_{1-4}$alkyl):

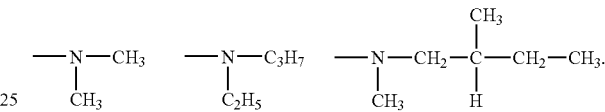

For the avoidance of doubt, in the definition of linker group 'X', the right hand side of the group is attached to phenyl ring and the left hand side is bound to 'Y'.

The invention includes the E and Z isomers of compounds of the invention defined above, but the preferred compounds are the E isomers. It is to be understood that, insofar as certain of the compounds of the invention may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form.

Preferred compounds of Formula (I) to (Ic) above or of Formula (II) to (IIf) below are those wherein any one or more of the following apply:

(1) m is 0 or 1;
  n is 1 or 2; preferably n is 2;
  most preferably m is 0 and n is 2.

(2) The $R^1$ and/or $R^2$ group(s) are attached at the 2-position and/or the 3-position and/or the 5-position; when n+m is 2, the groups are preferably at the 2- and 5- or 3- and 5-positions, most preferably at the 2- and 5- positions.

(3) each $R^1$ is independently selected from OH, $CH_{3-a}F_a$ (preferably $CF_3$), $OCH_{3-a}F_a$ (preferably $OCF_3$), halo, $C_{1-6}$alkyl (preferably methyl), $NO_2$ or heterocyclyl optionally substituted by C1-6alkyl, preferably $R_1$ is selected from $CH_{3-a}F_a$ (preferably $CF_3$), $OCH_{3-a}F_a$ (preferably $OCF_3$ ) or halo;

(4) each $R^2$ is the group Y—X—
  wherein each X is independently selected from:
    —O—Z—, —C(O)O—Z—, —S—Z—, —SO—Z—, —SO$_2$—Z—, —N(R$^6$)SO$_2$,Z— —SO$_2$NH—Z—, —(CH$_2$)$_{1-4}$—, —CH=CH—Z—, —C≡C—C—Z—, —N(R$^6$)CO—Z—, —CON(R$^6$)—Z— or a direct bond;

Preferably X is independently selected from:
—O—Z—, —S—Z—, —SO—Z—, —SO$_2$—Z, —N(R$^6$)SO$_2$, Z— —SO$_2$NH—Z— —(CH$_2$)$_{1-4}$— or a direct bond Most preferably X is independently selected from: —O—, —S—, —SO—, —SO$_2$—, —(CH$_2$)$_{1-4}$— or a direct bond;

each Z is independently selected from:
a direct bond or —(CH$_2$)$_{1-2}$, or a group of the formula —(CH$_2$)$_p$—C(R$^6$)$_2$—(CH$_2$)$_q$—, wherein one R$^6$ group is hydrogen and the other R$^6$ group is C$_{1-4}$alkyl;
preferably a direct bond, —(CH$_2$)$_{0-2}$— or

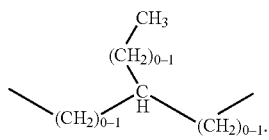

more preferably a direct bond or —CH$_2$—.

each Z$^1$ is independently selected from:
a direct bond, C$_{2-6}$alkenylene or a group of the formula —(CH$_2$)$_p$—C(R$^6$)$_2$—(CH$_2$)$_q$—, wherein one R$^6$ group is hydrogen and the other R$^6$ group is C$_{1-4}$alkyl;
preferably a direct bond, —(CH$_2$)$_0$—, C$_{2-4}$alkenylene or

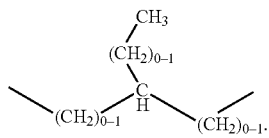

more preferably a direct bond, —(CH$_2$)$_{0-4}$—, 2-propenylene or

most preferably —(CH$_2$)$_{0-3}$—, 2-propenylene or a direct bond.

and each Y is independently selected from:
aryl-Z$^1$—, heterocyclyl-Z$^1$—, C$_{3-7}$cycloalkyl-Z$^1$—, C$_{1-6}$ alkyl, C$_{1-6}$alkoxy, C$_{2-6}$alkenyl or —CH(OH)CH$_{3-a}$F$_a$;
preferably each Y is independently selected from:
phenyl-Z$^1$—, heterocyclyl-Z$^1$—, C$_{3-7}$cycloalkyl-Z$^1$—, C$_{1-6}$ alkyl (preferably a branched C$_{2-6}$alkyl chain such as isopropyl or isobutyl), C$_{2-6}$alkenyl or —CH$_{3-a}$F$_a$;
most preferably Y is independently selected from:
phenyl-Z$^1$—, morpholinyl-Z$^1$—, pyridyl-Z$^1$—, pyrrolidino-Z$^1$—, isoxazolyl-Z$^1$—, diazolyl-Z$^1$—, furanyl-Z$^1$—, thienyl-Z$^1$—, thiazolyl-Z$^1$—, cyclopropyl-Z$^1$— or cyclohexyl-Z$^1$—,
wherein each Y is independently optionally substituted by R$^4$.

(5) each R$^2$ is the group Y—X, Z within the definition of X is a direct bond and Z$^1$ within the definition of Y is a group of the formula —(CH$_2$)$_p$—C(R$^6$)$_2$—(CH$_2$)$_q$—.

most preferably R$^2$ is independently selected from: methoxy, methylthio, methylsulphinyl, methylsulphonyl, ethoxy, iso-propoxy, pentyloxy, phenoxy, benzyloxy, phenylpropoxy, phenylallyloxy, phenylthio, diazolylmethoxy, diazolylethoxy, furanylmethoxy, isoxazolylmethoxy, morpholino, pyridylmethoxy, pyrrolidinylethoxy, thiazolyl, thiazolylmethoxy, thiazolyethoxy, thienylmethoxy, cyclopropylmethoxy, or cyclohexylmethoxy, wherein each of these R$^2$ groups is optionally substituted by R$^4$.

(6) each R$^4$ is independently selected from:
halo, —CH$_{3-6}$F$_a$, —OCH$_{3-a}$F$_a$, CN, NO$_2$, C$_{1-6}$alkyl, C$_{1-6}$alkoxy, —COOH, —(CH$_2$)$_{1-3}$COOH, —(CH$_2$)$_{0-3}$COOH, —C(O)phenyl, —C(O)NH$_2$, —C(O)NH-phenyl, —SO$_2$NH$_2$, —SO$_2$C$_{1-6}$alkyl, phenyl optionally substituted by C$_{1-6}$alkyl or —C(O)OC$_{1-6}$alkyl;
More preferably R$^4$ is independently selected from, chloro, bromo, fluoro, methyl, tert-butyl, isopropyl, methoxy, C$_{1-4}$alkoxycarbonyl, vinyl, CN, OH, trifluoromethyl, —COOH, —CH$_2$COOH, NO$_2$, methylsulphonyl, —C(O)NH$_2$, —C(O)NH-phenyl, —SO$_2$NH$_2$ or benzyloxy.

(7) R$^3$ is selected from hydrogen or C$_{1-6}$alkyl; preferably R$^3$ is selected from hydrogen or methyl; most preferably R$^3$ is hydrogen.

According to a further feature of the invention there is provided the following preferred groups of compounds of the invention.

(I) a compound of Formula (II)

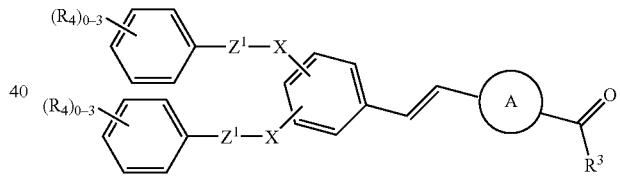

Formula (II)

wherein:

A, X, Z$^1$, R$^3$ and R$^4$ are as defined above in a compound of Formula (I); or a salt, solvate or pro-drug thereof.

(II) a compound of Formula (IIa)

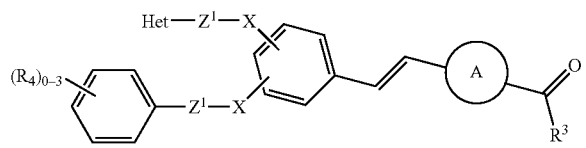

Formula (IIa)

wherein:

Het is a monocyclic heterocyclyl, optionally substituted with between 1 and 3 groups selected from R$^4$ and, A, X, Z$^1$, R$^3$ and R$^4$ are as defined above in a compound of Formula (I): or a salt, solvate or pro-drug thereof.

(III) a compound of Formula (IIb)

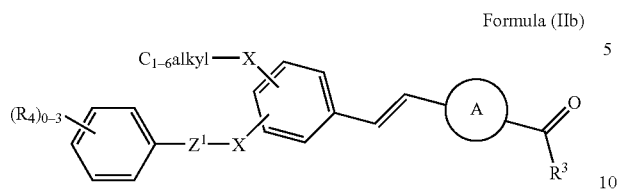

Formula (IIb)

wherein
  the $C_{1-6}$alkyl group is optionally substituted with between 1 and 3 groups selected from $R^4$, preferably unsubstituted;
  the $C_{1-6}$alkyl group optionally contains a double bond, preferably the $C_{1-6}$alkyl group does not contains a double bond; and
  A, X, $Z^1$, $R^3$ and $R^4$ are as defined above in a compound of Formula (I); with the proviso that:
  when A is pyridyl, $R^3$ is OH, phenyl-$Z^1$—X— is phenyl-$CH_2$—O— wherein the phenyl ring is unsubstituted, then $C_{1-6}$alkyl-X— must be other than $CH_3$—S— or $CH_3$—$SO_2$—; or a salt, solvate, or pro-drug thereof.

(IV) a compound of Formula (IIc)

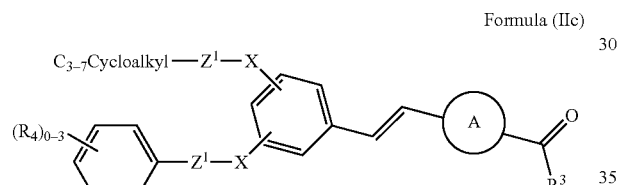

Formula (IIc)

wherein:
  the $C_{3-7}$cycloalkyl group is optionally substituted with between 1 and 3 groups selected from $R^4$, and
  A, X, $Z^1$, $R^3$ and $R^4$ are as defined above in a compound of Formula (I); or a salt, solvate or pro-drug thereof.

(V) a compound of Formula (IId)

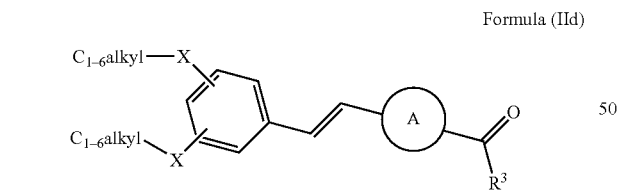

Formula (IId)

wherein:
  the $C_{1-6}$alkyl groups are independently optionally substituted with between 1 and 3 groups selected from $R^4$, preferably one of the $C_{1-6}$alkyl groups is unsubstituted, the $C_{1-6}$alkyl groups independently optionally contain a double bond, preferably only one of the $C_{1-6}$alkyl groups contain a double bond, preferably neither of the $C_{1-6}$alkyl group contains a double bond, and
  A, X, $R^3$ and $R^4$ are as defined above in a compound of Formula (I); with the proviso that A is other than pyridyl, furanyl or thiazolyl; or a salt, solvate or pro-drug thereof.

(VI) a compound of Formula (IIe)

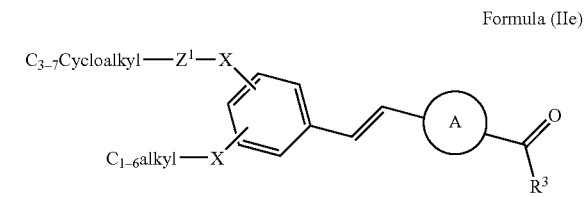

Formula (IIe)

wherein
  the $C_{1-6}$alkyl groups are independently optionally substituted with between 1 and 3 groups selected from $R^4$, preferably one of the $C_{1-6}$alkyl groups is unsubstituted, the $C_{1-6}$alkyl groups independently optionally contain a double bond, preferably only one of the $C_{1-6}$alkyl groups contain a double bond, preferably neither of the $C_{1-6}$alkyl group contains a double bond, and
  A, X, $R^3$ and $R^4$ are as defined above in a compound of Formula (I); with the proviso that A is other than pyridyl, furanyl or thiazolyl; or a salt, solvate or pro-drug thereof.

(VII) a compound of Formula (IIf)

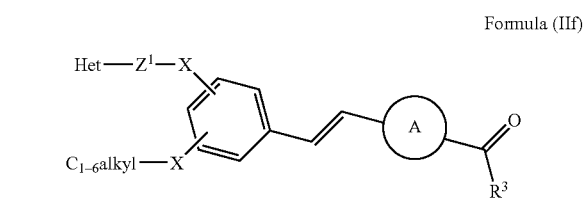

Formula (IIf)

wherein
  Het is a monocyclic heterocyclyl,
  the Het and $C_{1-6}$alkyl groups are independently optionally substituted with between 1 and 3 groups selected from $R^4$, preferably the $C_{1-6}$alkyl group is unsubstituted;
  the $C_{1-6}$alkyl group optionally contains a double bond, preferably the $C_{1-6}$alkyl group does not contains a double bond; and
  A, X, $Z^1$, $R^3$ and $R^4$ are as defined above in a compound of Formula (I); or a salt, solvate or pro-drug thereof.

(VIII) a compound of Formula (IIg)

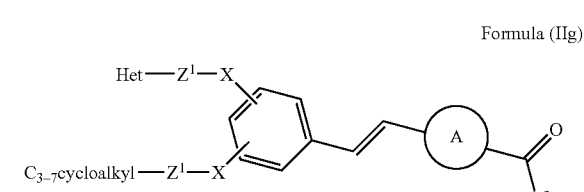

Formula (IIg)

wherein:
  Het is a monocyclic heterocyclyl,
  the Het and $C_{3-7}$cycloalkyl groups are independently optionally substituted with between 1 and 3 groups selected from $R^4$, and
  A, X, $Z^1$, $R^3$ and $R^4$ are as defined above in a compound of Formula (I); or a salt, solvate or pro-drug thereof.

(IX) a compound of Formula (IIh)

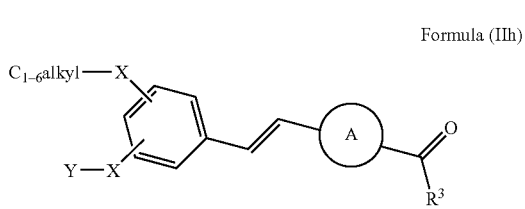

Formula (IIh)

wherein:
Y is aryl-$Z^1$—, wherein aryl is preferably a partially saturated bicyclic carbocyclic ring;
Y and the $C_{1-6}$alkyl group are independently optionally substituted with between 1 and 3 groups selected from $R^4$, preferably the $C_{1-6}$alkyl group is unsubstituted,
the $C_{1-6}$alkyl group optionally contains a double bond, preferably the $C_{1-6}$alkyl group does not contains a double bond; and
A, X, $Z^1$, $R^3$ and $R^4$ are as defined above in a compound of Formula (I); or a salt, solvate or pro-drug thereof.

(X) a compound of Formula (IIj)

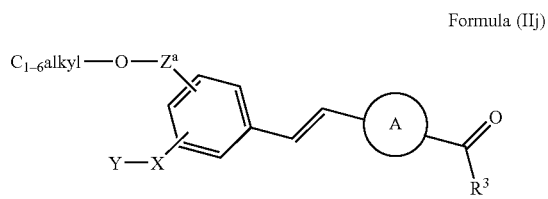

Formula (IIj)

wherein:
X is selected from —$SO_2N(R^6)$—Z— or —$N(R^6)SO_2$—Z—, preferably X is —$SO_2N(R^6)$—Z—;
Z is as described above, preferably Z is propylene, ethylene or methylene, more preferably Z is methylene;
$Z^a$ is selected from a direct bond or a group of the formula —$(CH_2)_p$—$C(R^6{}_2$—$(CH_2)_q$—; preferably $Z^a$ is selected from $C_{1-2}$alkylene or a direct bond; preferably $Z^a$ is a direct bond;
$R^6$ is selected from: $C_{1-4}$alkyl or hydrogen, preferably methyl or hydrogen;
Y is selected from aryl-$Z^1$— or heterocyclyl-$Z^1$—;
Y and the $C_{1-6}$alkyl group are independently optionally substituted with between 1 and 3 groups selected from $R^4$,
the $C_{1-6}$alkyl group optionally contains a double bond, preferably the $C_{1-6}$alkyl group does not contain a double bond, and
A, $Z^1$, $R^3$ and $R^4$ are as defined above in a compound of Formula (I); or a salt, solvate or pro-drug thereof.

A further preferred groups of compounds of the invention in either of groups (I)–(IX) above is wherein:
X is independently selected from —O—Z—, $SO_2N(R^6)$—Z— or —$N(R^6)$—Z—;
Z is a direct bond or —$CH_2$—;
$Z^1$ is selected from a direct bond, —$CH_2$———$(CH_2)_2$— or

$R^3$ is as defined above in a compound of Formula (I); or a salt, solvate or pro-drug thereof.

In a further embodiment of the invention there is provided a compound as defined in either of groups (I) to (X) above wherein:
A is selected from: pyridyl, pyrimidinyl, pyrazinyl, furanyl or thiazolyl; preferably A is linked to the styryl group at the 2-position of A.

In a further embodiment of the invention there is provided a compound as defined in either of groups (I) to (X) above wherein the two Y—X— groups are linked to the phenyl ring in a 2,5 orientation relative to the styryl group.

The compounds of the invention may be administered in the form of a pro-drug. A pro-drug is a bioprecursor or pharmaceutically acceptable compound being degradable in the body to produce a compound of the invention (such as an ester or amide of a compound of the invention, particular an in vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113–191 (1991);
d) H. Bundgaard, Advanced Drug Delivery Reviews, 8, 1–38 (1992);
e) H. Bundgaard, et al., Journal of Pharmaceutical Sciences, 77, 285 (1988); and
f) N. Kakeya, et al., Chem Pharm Bull, 32, 692 (1984).

The contents of the above cited documents are incorporated herein by reference.

Examples of pro-drugs are as follows. An in-vivo incorporated herein by reference compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $_6$alkanoyloxymethyl esters for example pivaloyloxymethyl, phthalidyl esters, $C_3$ to $_8$cycloalkoxycarbonyloxy$C_1$ to $_6$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2- dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, and ammonium salt or a salt with an organic base which affords a physiologically-acceptable cation, for example a salt with methylamine; dimethylamine, trimethylamine, piperidine, morpholine or tris-(2-hydroxyethyl)amine.

A further feature of the invention is a pharmaceutical composition comprising a compound of Formula (I) to (Ic) or (II) to (IIj) as defined above, or a salt, solvate or prodrug thereof, together with a pharmaceutically-acceptable diluent or carrier.

According to another aspect of the invention there is provided a compound of Formula (Ib) or (Ic), or (II) to (IIj) as defined above for use as a medicament; with the proviso that (i) when A is pyridyl or thiazolyl, m is 1 or 2 and n is 0, $R^3$ is OH or —O-$C_{1-6}$alkyl, then $R^1$ is other than halo, amino or nitro;

(ii) when A is pyridyl m=0, n=1, X is —N(CH$_3$)— or —N(CH$_3$)—CH$_2$—, $R^3$ is OH, then Y cannot be methyl;

(iii) when A is thiazolyl. m is 0, $R^3$ is OH, then when n is 2 $(R^2)_n$ cannot be di-$C_{1-6}$alkyl-O— or $C_{1-6}$alkyl-O-$C_{1-6}$alkenyl-O— and when n is 3 $(R^2)_n$ cannot be tri-$C_{1-6}$alkyl-O—;

(iv) when A is pyridyl, m is 0 or m is 1 and $R^1$ and $R^1$ is halo, n is 1 and $R^2$ is phenyl-CH$_2$—O—, then $R^3$ cannot be OH; and (v) when A is pyridyl, $R^3$ is OH, m is 0, n is 2 and one of the $R^2$ groups is phenyl-CH$_2$—O—, then the other $R^2$ group must be other than CH$_3$—S— or CH$_3$—SO$_2$—.

Further according to the invention there is provided a compound of Formula (Ib) or (Ic), or (II) or (IIj) for use in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (Ib) or (Ic), or (II) to (IIj) to a mammal in need of such treatment.

Specific disease which may be treated by the compound or composition of the invention include: blood glucose lowering in Diabetes Mellitus type 2 without a serious risk of hypoglycaemia (and potential to treat type 1), dyslipidemea, obesity, insulin resistance, metabolic syndrome X, impaired glucose tolerance.

Specific disease which may be treated by the compound or composition of the invention include: blood glucose lowering in Diabetes Mellitus type 2 (and potential to treat type 1); dyslipidaemia; obesity; insulin resistance; metabolic syndrome X; impaired glucose tolerance; polycystic ovary syndrome.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing.)

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl-p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or n a mineral agent such as beeswax, hard paraffin or cetyl alcohol. Sweetening agents such as those set out above, and flavouring agents may be added to provide a palatable oral preparation. These compositions may be preserved by the addition of an antioxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally occurring phosphatides such as soya bean, lecithin, an esters or partial esters derived from fatty acids and hexitol anhydrides (for example sorbitan monooleate) and condensation products of the said partial esters with ethylene oxides such as polyoxyethylene sorbitan monooleate. The emulsions may also containing sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the does for therapeutic or prophylactic purposes of a compound of the Formula (I), (Ia), (Ib) or (Ic) will naturally vary according to the nature and severity of the conditions, the age and sex of the animal or patient and the route of administration, according to well known principles of medicine.

In using a compound of the Formula (I), (Ia), (Ib) or (Ic) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;
2) Insulin secretagogues including sulphonylureas (for example gibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti-dyslipidaemia agents such as, HMG-CoA reductase inhibitors (statins, eg pravastatin); PPAR$\alpha$ agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, $\beta$ blockers (eg atenolol, inderal); ACE inhibitors (eg lisinopril); Calcium antagonists (eg. nifedipine); Angiotensin receptor antagonists (eg candesartan), $\alpha$ antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts thereof.

A compound of the invention, or a salt, pro-drug or solvate thereof, may be prepared by any process known to be applicable to the preparation of such compounds or structurally related compounds. Such processes are illustrated by the following representative schemes (1 to 4) in which variable groups have nay of the meanings defined for Formula (I) unless stated otherwise and A is for example depicted as pyridyl. Functional groups may be protected and deprotected using conventional methods.

For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991. Note abbreviations used have been listed immediately before the Examples below.

SCHEME 1

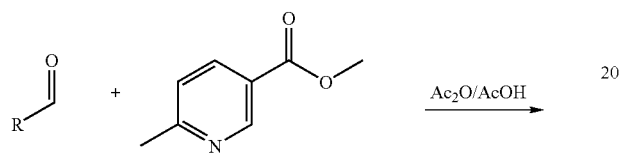

-continued

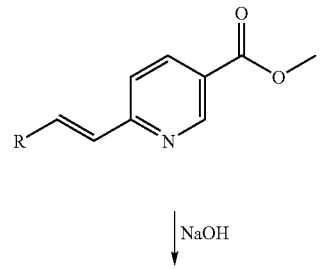

SCHEME 2

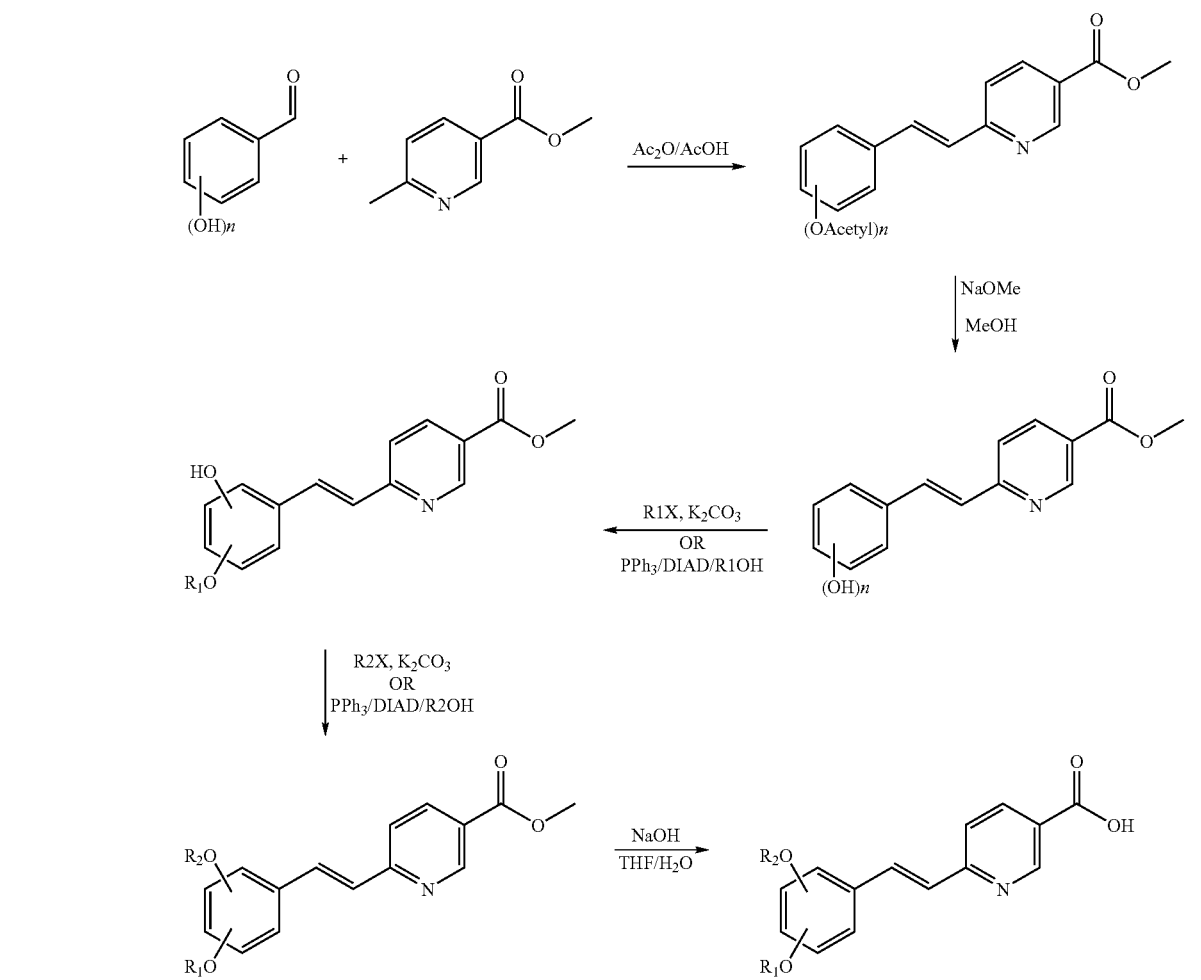

n = 1, 2

-continued

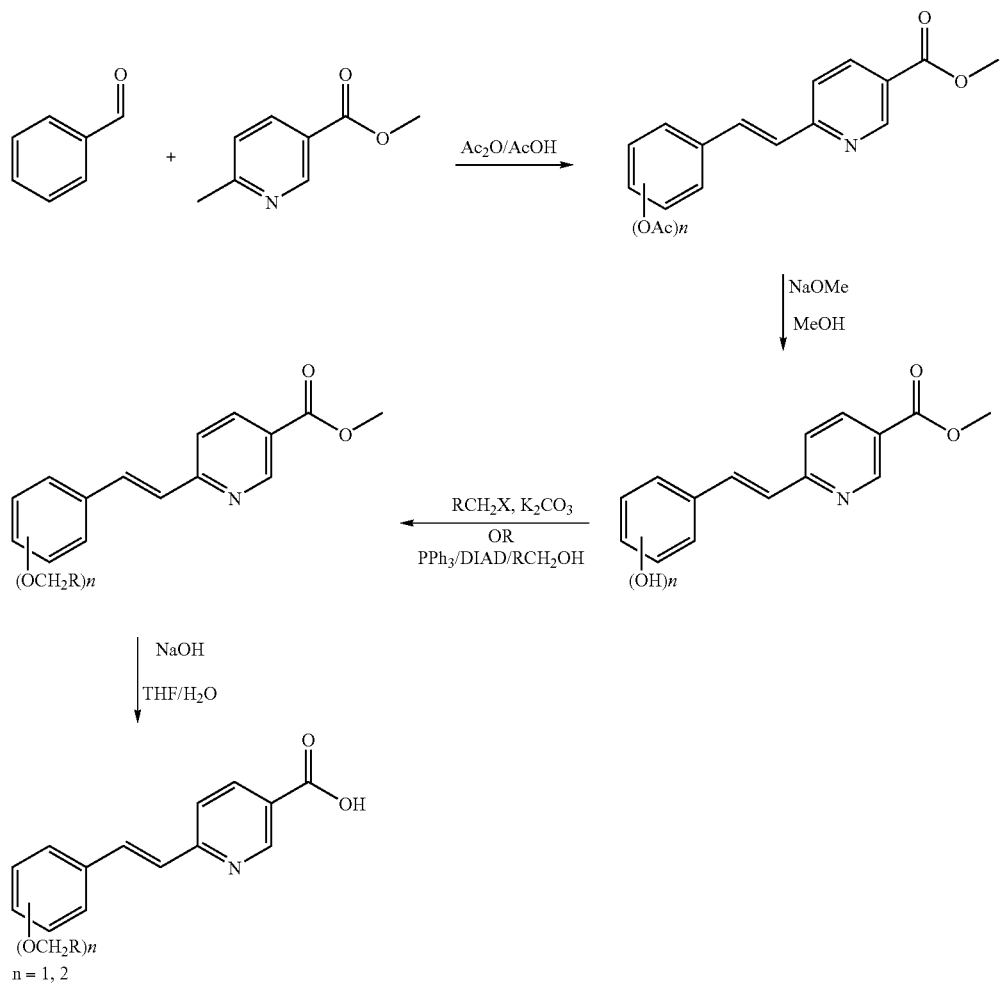

SCHEME 4

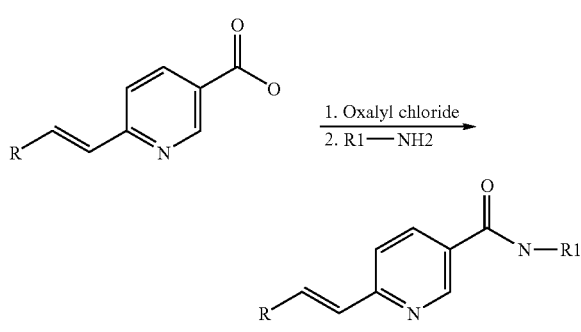

During the preparation process, it may be advantageous to use a protecting group for a functional group within the molecule. Protecting groups may be removed by any convenient method as described in the literature or known to the skilled chemist and appropriate for the removal of the protecting group in question, such methods being chosen so as to effect removal of the protecting group with minimum disturbance of groups elsewhere in the molecule.

Processes for the synthesis of compounds of Formula (I) are provided as a further feature of the invention. Thus, according to a further aspect of the invention there is provided a process for the preparation of a compound of Formula (I) which comprises:

(a) reaction of a compound of Formula (IIa) with a compound of Formula (IIIb),

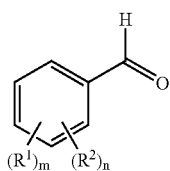

Formula (IIIa)

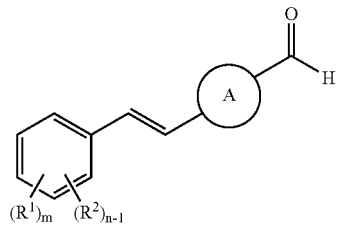

Formula (IIIf)

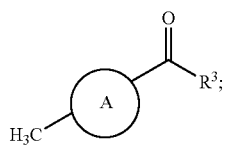

Formula (IIIb)

$H_2N-R^6$;

Formula (IIIg)

(b) for compounds of Formula (I) wherein $R^3$ is hydrogen, de-protection of a compound of Formula (IIIc), and thereafter, if necessary:
i) converting a compound of Formula (I) into another compound of Formula (I);
ii) removing any protecting groups;
iii) forming a salt, pro-drug or solvate thereof.

Specific reaction conditions for the above reactions are as follows:

Process a)—as described above in Scheme 1;
Process b)—as described above in Scheme 1/2
Process c)—examples of this process are as follows:

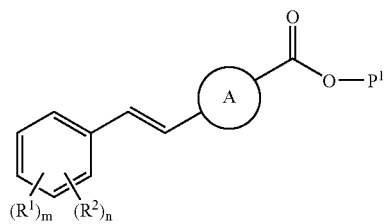

Formula (IIIc)

wherein $P^1$ is a protecting group;

(c) reaction of a compound of Formula (IIId) with a compound of Formula (IIIe),

Y—X″

Formula (IIId)

Formula (IIIe)

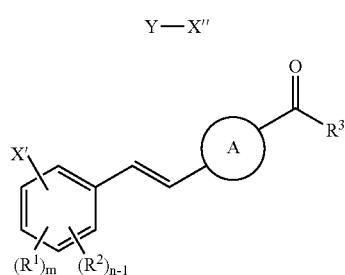

wherein X' and X″ comprises groups which when reacted together form the group X;

(d) for a compound of Formula (I) wherein X or $X^1$ is —SO—Z—, —SO$_2$—Z—, oxidation of the corresponding compound of Formula (I) wherein X or $X^1$ respectively is —S—Z—; or (e) for a compound of Formula (I) wherein $R^3$ is NHR$^6$, reaction of a compound of Formula (IIIf) with a compound of Formula (IIIg), (i) to form a group when X is —O—Z—, X' is a group of formula HO—Z— and X″ is a leaving group (alternatively X' is a group of formula $L^2$—Z— wherein $L^2$ is a leaving group and X″ is a hydroxyl group), compounds of Formula (IIId) and (IIIe) are reacted together in a suitable solvent, such as DMF or THF, with a base such as sodium hydride or potassium tert-butoxide, at a temperature in the range 0 to 100° C., optionally using metal catalysis such as palladium on carbon or cuprous iodide;

(ii) to form a group when X is $N(R^6)$—Z—, X' is a group of formula H—(R$^6$)N—Z— and X″ is a leaving group (alternatively X' is a group of formula $L^2$—X— wherein $L^2$ is a leaving group and X″ is a group or formula —N(R$^6$)—H), compounds of Formula (IIId) and (IIIe) are reacted together in a suitable solvent such as THF, an alcohol or acetonitrile, using a reducing agent such as sodium cyano borohydride or sodium trisacetoxyborohydride at room temperature;

(iii) to form a group when X is —SO$_2$N(R$^6$)—Z—, X' is a group of formula H—N(R$^6$)—Z— wherein $L^2$ is a leaving group and X″ is an activated sulphonyl group such as a group of formula —SO$_2$—Cl, compounds of Formula (IIId) and (IIIe) are reacted together in a suitable solvent such as methylene chloride, THF or pyridine, in the presence of a base such as triethylamine or pyridine at room temperature;

(iv) to form a group when X is —N(R$^6$)SO$_2$—Z—, X' is an activated sulphonyl group such as a group of formula Cl—SO$_1$—Z— group and X″ is a group of formula —N(R$^6$)—$L^2$ wherein $L^2$ is a leaving group, compounds of Formula (IIId) and (IIIe) are reacted together in a suitable solvent such as methylene chloride, THF or pyridine, in the presence of a base such as triethylamine or pyridine at room temperature;

(v) to form a group when X is —C(O)N(R$^6$)—Z—, X' is a group of formula H—N(R$^6$)—Z— wherein $L^2$ is a leaving group and X" is an activated carbonyl group such as a group of formula —C(O)—Cl, compounds of Formula (IIId) and (IIIe) are reacted together in a suitable solvent such as THF or methylene chloride, in the presence of a base such as triethylamine or pyridine at room temperature;

(vi) to form a group when X is —N(R$^6$)C(O)—Z—, X' is an activated carbonyl group such as a group of formula Cl—C(O)—Z— group and X" is a group of formula —N(R$^6$)—L$^2$ wherein L$^2$ is a leaving group, compounds of Formula (IIId) and (IIIe) are reacted together in a suitable solvent such as THF or methylene chloride, in the presence of a base such as triethylamine or pyridine at room temperature;

(vii) to form a grouped when X is —CH═CH—Z—, a Wittag reaction or a Wadsworth-Emmans Horner reaction can be used. For example, X' terminates in an aldehyde group and Y—X" is a phosphine derivative of the formula Y—C$^-$H—P$^+$PH$_3$ which can be reacted together in a strong base such as sodium hydride or potassium tert-butoxide, in a suitable solvent such as THF at a temperature between room temperature and 100° C.

Process d)—the oxidization of a compound of Formula (I) wherein X or X$^1$ is —S—Z— is well known in the art, for example, reaction with metachloroperbenzoic acid (MCPBA) is the presence of a suitable solvent such as dichloromethane at ambient temperature. If an excess of MCPBA is used a compound of Formula (I) wherein X is —S(O$_2$)— is obtained.

Process e)—as described above in Scheme 4.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms). Examples of carboxy protecting groups include straight or branched chain (C$_{1-12}$)alkyl groups (e.g. isopropyl, t-butyl); lower alkoky lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g., p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, base, metal- or enzymically-catalysed hydrolysis, or photolytically for groups such as o-nitrobenzyloxycarbonyl, or with fluoride ions for silyl groups.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

The present invention also relates to the use of a GLK activator for the combined treatment of diabetes and obesity. GLK and GLKRP and the K$_{ATP}$ channel are expressed in neurones of the hypothalamus, a region of the brain that is important in the regulation of energy balance and the control of food intake [14–18 . These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23–28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

This according to a second aspect of the invention there is provided the use of a GLK activator in the preparation of a medicament for the combined treatment or prevention of diabetes and obesity.

According to a further feature of the second aspect of the invention there is provided a method of combined treatment, in a warm-blooded animal, of diabetes and obesity, comprising administering a therapeutically effective amount of a compound of a GLK activator, or a pharmaceutically-acceptable salt, pro-drug or solvate thereof.

According to a further feature of the second aspect of the invention there is provided a pharmaceutical composition comprising a GLK activator, or a pharmaceutically acceptable salt, prodrug or solvate thereof, in admixture with a pharmaceutically-acceptable diluent or carrier for the combined treatment of diabetes and obesity in a warm-blooded animal.

According to a further feature of the second aspect of the invention there is provided to use a GLK activator in the preparation of a medicament for the treatment or prevention of diabetes and obesity, wherein the GLK activator is a compound of Formula (I) above.

According to a further feature of the second aspect of the invention there is provided a method of combined treatment, in a warm-blooded animal, of diabetes and obesity, comprising administering a therapeutically effective amount of a compound of a GLK activator, or a pharmaceutically-acceptable salt, pro-drug or solvate thereof, wherein the GLK activator is a compound of Formula (I) above.

According to a further features of the second aspect of the invention there is provided a pharmaceutical composition comprising a GLK activator, or a pharmaceutically acceptable salt, prodrug or solvate thereof, in admixture with a pharmaceutically-acceptable diluent or carrier for the combined treatment of diabetes and obesity in a warm-blooded animal, wherein the GLK activator is a compound of Formula (I) above.

According to a further feature of the second aspect of the invention there is provided the use of a GLK activator in the preparation of a medicament for the treatment or prevention of diabetes and obesity, wherein the GLK activator is a compound of Formula (IV) below.

Formula (IV)

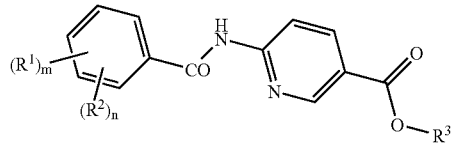

wherein
m is 0, 1 or 2;
n is 0, 1, 2, 3 or 4;
and n+m>0;
each $R^1$ is independently selected from OH, —$(CH_2)_{1-4}$OH, —$CH_{3-a}F_a$, —$(CH_2)_{1-4}CH_{3-a}F_a$, halo, $C_{1-6}$alkyl, $C_{2-6}$alkenyl, $C_{2-6}$alkynyl, $NO_2$, $NH_2$, —NH—$C_{1-4}$alkyl, —N-di-($C_{1-4}$alkyl), CN or formula;
each $R^2$ is the group Y—X—
wherein each X is a linker independently selected from:
—O—Z—, —O—Z—O—Z, —C(O)O—Z—, —OC(O)—Z—, —S—Z—, —SO—Z—, —$SO_2$—Z—, —N($R^6$)—Z—, —N($R^6$)$SO_2$—Z, —$SO_2$N($R^6$)—Z—, —$(CH_2)_{1-4}$—, —CH=CH—Z—, —C≡C—Z—, —N($R^6$)CO—Z—, —CON($R^6$)—Z—, —C(O)N($R^6$)S(O)$_2$—Z—, —S(O)$_2$N($R^6$)C(O)—Z—, —C(O)—Z— or a direct bond;
each Z is independently a direct bond or a group of the formula —$(CH_2)_p$—C($R^6$)$_2$—$(CH_2)_q$—;
each Y is independently selected from aryl-$Z^1$—, heterocyclyl-$Z^1$—, $C_{3-7}$cycloalkyl-$Z^1$—, $C_{1-6}$alkyl, $C_{2-6}$alkenyl, $C_{2-6}$alkynyl or —$(CH_2)_{1-4}CH_{3-a}F_a$;
wherein each Y is independently optionally substituted by up to 3 $R^4$ groups;
each $R^4$ is independently selected from halo, —$CH_{3-a}F_a$, CN, $NO_2$, $NH_2$, $C_{1-6}$alkyl, —$OC_{1-6}$alkyl, —COOH, —C(O)O$C_{1-6}$alkyl, OH or phenyl,
or $R^5$—$X^1$—, where $X^1$ is independently as defined in X above and $R^5$ is selected from hydrogen, $C_{1-6}$alkyl, —$CH_{3-a}F_a$, phenyl, naphthyl, heterocyclyl or $C_{3-7}$cycloalkyl; and $R^5$ is optionally substituted by halo, $C_{1-6}$alkyl, —$CH_{3-a}F_a$, CN, $NO_2$, $NH_2$, COOH or —C(O)O$C_{1-6}$alkyl,
wherein each phenyl, naphthyl or heterocyclyl ring in $R^5$ is optionally substituted by halo, $CH_{3-a}F_a$, CN, $NO_2$, $NH_2$, $C_{1-6}$alkyl, —$OC_{1-6}$alkyl, COOH, —C(O)O$C_{1-6}$alkyl or OH;
each $Z^1$ is independently a direct bond or a group of the formula —$(CH_2)_p$—C($R^6$)$_2$—$(CH_2)_q$;
$R^3$ is selected from hydrogen or $C_{1-6}$alkyl; and
$R^6$ is independently selected from hydrogen, $C_{1-6}$alkyl or —$C_{2-4}$alkyl-O-$C_{1-4}$alkyl;
each a is independently 1,2 or 3;
p is an integer between 0 and 2;
q is an integer between 0 and 2;
and p+q<4.

According to a further feature of the second aspect of the invention there is provided a method of combined treatment, in a warm-blooded animal, of diabetes and obesity, comprising administering a therapeutically effective amount of a compound of a GLK activator, or a pharmaceutically-acceptable salt, pro-drug or solvate thereof, wherein the GLK activator is a compound of Formula (IV).

According to a further feature of the second aspect of the invention there is provided a pharmaceutical composition comprising a GLK activator, or a pharmaceutically acceptable salt, prodrug or solvate thereof, in admixture with a pharmaceutically-acceptable diluent or carrier for the combined treatment of diabetes and obesity in a warm-blooded animal, wherein the GLK activator is a compound of Formula (IV).

Further examples of GLK activators are contained in International Application numbers: WO 00/58293, WO 01/44216, WO 01/83465, WO 01/83478, WO 01/85706, WO 01/85707, WO 02/08209 and WO 02/14312. The contents of aforesaid International Applications are hereby incorporated by reference.

In a further feature of the second aspect of the invention there is provided the use of a GLK activator in the preparation of a medicament for the treatment or prevention of diabetics and obesity, wherein the GLK activator is a compound exemplified in aforesaid International Applications or falls within the scope of aforesaid International Applications.

According to a further feature of the second aspect of the invention there is provided a method of combined treatment, in a warm-blooded animal, of diabetes and obesity, comprising administering a therapeutically effective amount of a compound of a GLK activator, wherein the GLK activator is a compound exemplified in aforesaid International Applications or falls within the scope of aforesaid International Applications.

According to a further feature of the second aspect of the invention there is provided a pharmaceutical composition comprising a GLK activator, or a pharmaceutically acceptable salt, prodrug or solvate thereof, in admixture with a pharmaceutically-acceptable diluent or carrier for the combined treatment of diabetes and obesity in a warm-blooded animal, wherein the GLK activator is a compound exemplified in aforesaid International Applications or falls within the scope of aforesaid International Applications.

The identification of compounds that are useful in the combined treatment of diabetes and obesity is the subject of the present invention. These properties may be assessed, for example, by measuring changes in food intake, feeding-related behaviour (eg. feeding, grooming, physical activity, rest) and body weight separately or together with measuring plasma or blood glucose or insulin concentrations with or without an oral glucose load/food in a variety of animal models such as ob/ob mouse, db/db mouse, Fatty Zucker rat, Zucker diabetic rate (ZDF), a streptozotocin-treated rats or mice or diet-induced obese mice or rats, as described in Sima & Shafrir, 2001, Animal Models of Diabetes. A Primer (Harwood Academic Publishers, Netherlands) or in animals treated with glucose directly into the brain or in animals rendered diabetic by treatment with streptozotocin and fed a high fat diet (Metabolism 49: 1390–4, 2000).

GLK activators may be used in the combined treatment of diabetes and obesity alone or in combination with one or more additional therapies. Such combination therapy may be achieved by way of the simultaneous, sequential or separate administration of the individual components of the treatment. Simultaneous treatment may be in a single table or in separate tablets. Examples of agents which may be used in combination therapy include those listed in paragraphs 1)–11) above, as drugs which may be used with compounds of Formula (I).

The following examples of Compounds of Formula (I)–(Ic) are for illustration purposes and are not intended to limit the scope of this application. Each exemplified compound represents a particular and independent aspect of the invention. In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18–25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Silica gel 60, 0.040–0.063 mm, 230–400 mesh); and (vi) Biotage cartridges refer to pre-packed silica cartridges (from 40 g up to 400 g), eluted using a biotage pump and fraction collector system; Biotage UK Ltd, Hertford, Herts, UK.

EXAMPLE A

Scheme 1: Preparation of
6-(E-3-phenoxy-phenyl]-vinyl)-nicotinic Acid

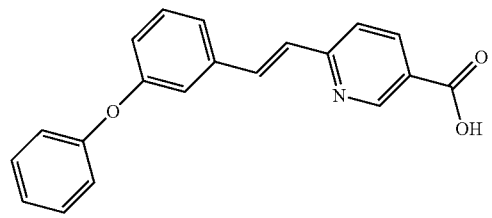

To a mixture of 6- methylnicotinate (151 mg, 1 mmol), acetic anydride (541 mg, 5.3 mmol) and acetic acid (52 mg, 0.87 mmol) was added 3-(hydroxybenzyl)benzaldehyde (201 mg, 1.01 mmol). The reaction was heated to 120° C. for 24 hours and was then cooled to room temperature before ethyl acetate (5 ml) and water (5 ml) were added. The biphasic mixture was separated and the organic phase was washed with an aqueous saturated solution of sodium bicarbonate (5 ml). The organic phase was then filtered through magnesium sulfate absorbed onto silica gel and was concentrated in vacuo. The crude product was chromatographed on Kieselgel 60, eluting with a gradient of 10–40% ethyl acetate in iso-hexane to give the product as a white solid (162 mg, 49% yield); MS [M+H]·332.

The product from the previous step (162 mg) was dissolved in a mixture of THF (2.5 ml) and 1 M aqueous NaOH solution (1.25 ml) and was then heated for 2 hours at 60° C. The reaction was allowed to cool to room temperature overnight and was the reduced in vacuo to remove the THF. 1 N aqueous HCl was added to precipitate out 6-(E-3-phenoxy-phenyl]-vinyl)-nicotinic acid which was isolated by filtration as a white solid (117 mg, 76% yield); H$^1$ NMR δ (d$^6$-DMSO) 6.95–7.85 (12 H, m), 8.25 (1 H, dd), 9.05 (1 H, d) 13.30 (1 H, br, s); MS [M+H]·318.

EXAMPLE B

Scheme 2: Preparation Of 6-(E-2-[-2-(4-isopropyl-benzyloxy)-5-methylsulfanyl-phenyl]-vinyl-nicotinic Acid

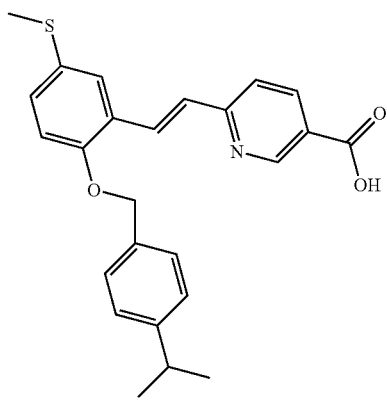

Sodium hydride (160 mg, 60% w/w in mineral oil, 4 mmol) was added to a solution containing 4-isopropylbenzyl chloride (350 µL, 2.1 mmol) and 6-[E-2-(-2-hydroxy-5-methylsulfanylphenyl)-vinyl]-nicotinic acid, methyl ester (600 mg, 2 mmol) in DMF (20 mL). The mixture was stirred overnight at room temperature. The reaction mixture was concentrated in vacuo and the residue was dissolved in THF (10 mL). Methanol (4 mL) and aqueous sodium hydroxide (4 mL, 1 M) were added the solution was stirred at room temperature for 5 hours. The reaction mixture was concentrated in vacuo before being dissolved in water (10 mL). This solution was acidified with hydrochloric acid (1 M) and the resulting precipitate was isolated by filtration, washed with water and dried in vacuo. The product was obtained as a yellow solid (880 mg, quant.) $\delta_H$ (300 MHz, DMSO-d$_6$) 13.2 (1 H, s), 9.01 (1 H, d), 8.22 (1 H, dd), 8.04 (1 H, d), 7.66 (1 H, d), 7.53 (1 H, d), 7.45 (1 H, d), 7.39 (2 H, d), 7.29–7.20 (3 H, m), 7.11 (1 H, d), 5.18 (4 H, s), 2,87 (1 H, septet), 2.51 (3 H and residual DMSO-d$_5$, s), and 1.19 (6 H, d); m/z (LCMS) (ESI+) 420 (MH+); (ESI—) 418 (M—H).

EXAMPLE C

Scheme 2: Preparation of 6-[E-2-(-2-hydroxy-5-methylsulfanylphenyl)-vinyl]-nicotinic Acid, Methyl Ester Sodium methoxide (2.29 g, 42.4 mmol) was added to a suspension of 6-[E-2-(-2-acetoxy-5-methylsulfanylphenyl)-vinyl]-nicotinic acid, methyl ester (13.26 g, 38.55 mmol) in methanol (200 mL). The mixture was heated at 60° C. for 3 hours. The reaction mixture was concentrated in vacuo and water was added followed by enough hydrochloric acid (1 M) to acidify the solution. The resultant precipitate was isolated by filtration, washed with water and dried in vacuo. This procedure afforded the product as a yellow solid (8.8 g, 76%) m/z (LCMS) (ESI+) 302 (MH+); (ESI–) 300 (M—H).

EXAMPLE D

Scheme 2: Preparation of 6-[E-2-(-2-acetoxy-5-methylsulfanylphenyl)-vinyl]-nicotinic Acid, Methyl Ester 2-hydroxy-5-methylsulfanylbenzaldehyde (5.05 g, 30 mmol) was dissolved in acetic anhydride (8 mL). Methyl 6-methylnicotinate (4.54 g, 30 mmol) and acetic acid (1.7 mL, 30 mmol) were added. The mixture was heated to 120° C. and stirred for 18 hours. The mixture was allowed to cool to room temperature before being poured into water (200 mL). The aqueous mixture was extracted with ethyl acetate (200 mL). The extract was washed with brine, dried over magnesium sulfate and concentrated in vacuo to afford a brown solid. This material was triturated with ethanol to give 6-[E-2-(-2-acetoxy-5-methylsulfanylphenyl)-vinyl]-nicotinic acid, methyl ester as a colourless solid (7.33 g, 71%) $\delta_H$ (300 MHz, DMSO-d$_6$) 9.06 (1 H, d), 8.28 (1 H, dd), 7.77–7.68 (3 H, m), 7.50 (1 H, d), 7.27 (1 H, d), 7.15 (1 H, d), 3.86 (3 H, s), 2.55 (3 H, s), and 2.36 (3 H, s); m/z (ESI+) 344 (MH+).

EXAMPLE E

Scheme 3: Preparation of

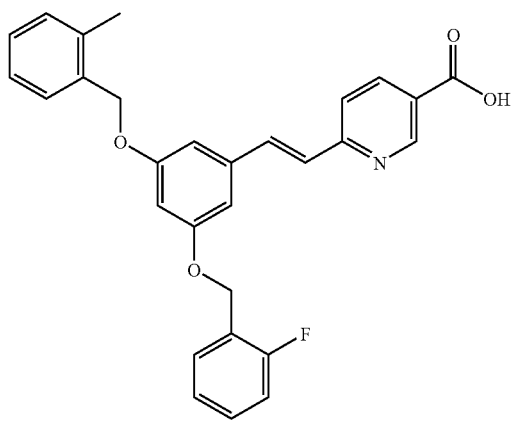

Compound (a) (260 mg 0.69 mm) was stirred with potassium carbonate (286 mg 2.07 mm), potassium iodide (catalytic) and 2-methylbenzyl bromide (0.101 ml 0.76 mm) in dimethylformamide at 60° C. overnight.

Compound (a)

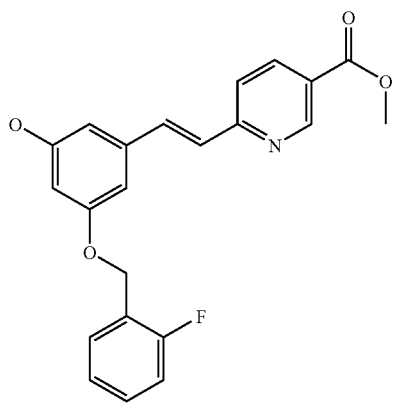

Compound (b) (9.65 g 35.61 mm) was stirred with 2-fluorobenzyl bromide (4.29 ml 35.61 mm), potassium carbonate (14.74 g 106.83 mm) potassium iodide (1.0 g 6 mm catalytic) in dimethylformamide (40 ml).

Compound (b)

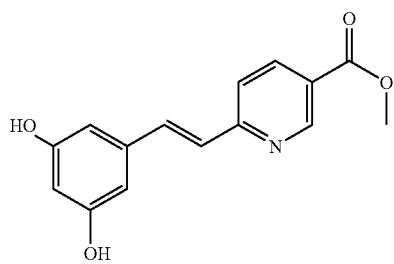

Water (5 ml) was added to the cooled reaction and the mixture was filtered, washed well with water and dried under vacuum at room temperature. The compound was purified by bond elute chromatography, eluting with 20% ethyl acetate/isohexane. The product from this column was stirred with 2 N sodium hydroxide (1.725 ml 3.45 mm) in tetrahydrofuran (4 ml) methyl alcohol (2 ml) and water (2 ml) for 3 hours at room temperature. The mixture was then evaporated to dryness, diluted with water and acidified with 2 N hydrochloric acid to give a precipitate. The precipitate was filtered off, washed well with water and dried at room temperature under vacuum to give the product. (270 mg, 83.4%) Nmr dmso-$d_6$ (d) 2.34 (3 H, s), 5.11–5.23 (4 H d) 6.72 (1 H s) 7.05 (2 H s) 7.15–7.35 (5 H m) 7.4–7.5 (3 H m) 7.55–7.65 (2 H m) 7.68–7.78 (1 H d) 8.18–8.23 (1 H d) 9.03 (1 H s) M.S.—MH$^+$ 470.

After cooling, the mixture was poured into water and extracted into ethyl acetate. The combined organic extracts were dried over magnesium sulphate, filtered and evaporated to give the crude product. Chromatography on silica using 0.6% methanol/methylene chloride, followed by 10% methanol/methylene chloride gave the pure product (1.89 g 14%). M.S. MH$^+$ 380.

EXAMPLE G

Scheme 3: Preparation of

EXAMPLE F

Scheme 3: Preparation of

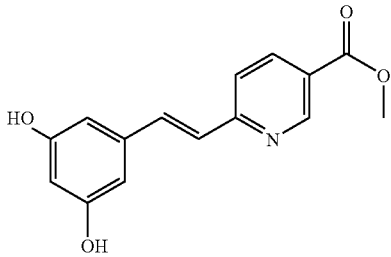

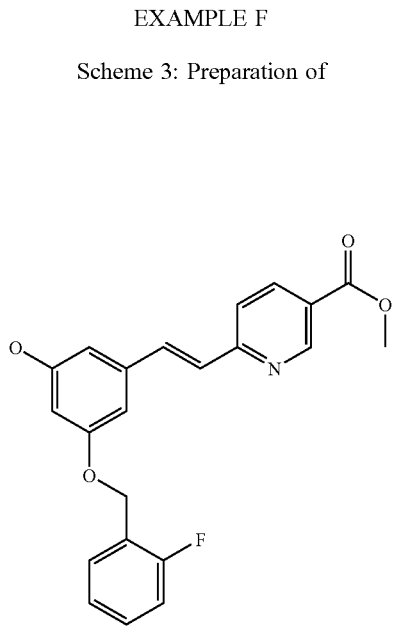

The diacetyl derivitive (15.36 g 43 mm) of the structure above was stirred at room temperature with 4 N sodium methoxide (9.8 ml 43 mm) in tetrahydrofuran (10 ml) and methanol (10 ml) for 1 hour. The mixture was evaporated diluted with water and acidified with hydrochloric acid. The resulting precipitate was filtered off washed with water and vacuum dried at 50° C. to give the product (11.2 g 96.1%) MS MH$^+$ 272

EXAMPLE H

Scheme 3: Preparation of

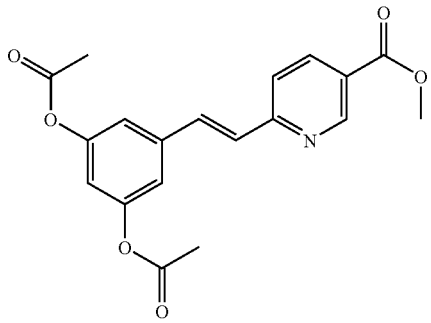

3,5-Dihydroxybenzaldehyde (10 g 72.46 mm) was stirred with 6-methyl methyl nicotinate (10.94 g 72.46 mm) in acetic acid (3.7 ml 65 mm) and acetic anydride (37 ml 0.39 m) at 120° C. overnight. On cooling the brown solid mixture was diluted with ethyl acetate. The insoluble material was filtered off and washed with ethyl acetate to give the product (15.36 g) The remaining organic solubles were washed with water and then added to sodium bicarbonate and the solid filtered off washed with water and vacuum dried(1.78 g). Both the solids were identical and so were combined to give the final product (17.14 g 66.6%) MS MH$^+$356.

EXAMPLE I

Scheme 4: Preparation of 6-(E-2-[-2-(2-benzyloxy)-5-methylsulfanyl-phenyl]-vinyl)-nicotinic Acid, Methyl Sulphonamide To a suspension of Compound (c) (100 mg) in dichloromethane (10 ml) was added methanesulfonamide (38 mg), 4-dimethylaminopyridine (130 mg), then 1-(3-dimethylaminopropyl)-3-ethylcarbodiimide hydrochloride (102 mg). The mixture was stirred for 20 hours at ambient temperature. Diluted with dichloromethane (20 ml), washed with 2 M hydrochloric acid (10 ml), brine (15 ml), and dried over Magnesium sulfate. Volatile material was removed by evaporation to give the title product (112 mg), as a solid.

$^1$HNMR (CLCl$_3$) 2.48 (s, 3 H), 3.43 (s, 3 H), 5.20 (s, 2 H), 6.92 (d, 1 H), 7.25 (m, 1 H+CDCl$_3$), 7.33–7.48 (m, 7 H), 7.57 (d, 1 H), 7.60 (s, 1 H), 8.13 (d, 1 H), 8.32 (d, 1 H), 9.26 (s, 1 H), MS ES$^+$ 455.13 (M+H)$^+$.

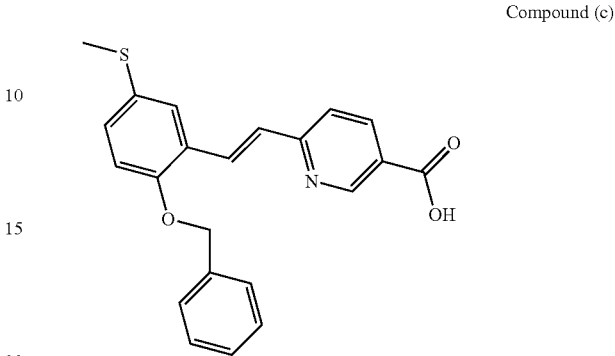

Compound (c)

EXAMPLE J

By analagous methods to those described compounds J$_{1-127}$ listed in Table 1 were also made. Table 2 gives the parent molecular weight, mass spec data and the synthetic scheme for the compounds listed in Table 1.

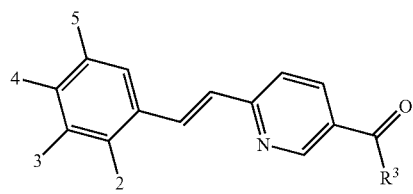

In compounds 1–114 R$^3$ is OH; in compound 115–123 R$^3$ is methoxy; in compound 124 R$^3$ is methylsulphonylamino; in compounds 125 R$^3$ is methoxyamino; in compounds 126–127 R$^3$ is 2-hydroxyethylamide.

Compound 2 corresponds to the product of Example A. Compound 36 corresponds to the product of Example B. Compound 101 corresponds to Example E. Compound 124 corresponds to the product of Example I.

TABLE 1

| Compound number | 2 | 3 | 4 | 5 |
|---|---|---|---|---|
| 1 | H | Methylthio | H | H |
| 2 | H | Phenoxy | H | H |
| 3 | H | CF$_3$ | H | CF3 |
| 4 | H | Benxyloxy | H | H |
| 5 | OH | Br | H | Br |
| 6 | 4-ChloroPhenylthio | H | H | NO2 |
| 7 | 4-MethylPhenylthio | H | H | NO2 |
| 8 | Chloro | H | H | Ethoxy |
| 9 | Chloro | H | H | Chloro |
| 10 | Chloro | H | H | CF3 |
| 11 | H | H | (5-t-Butyl)-thiazol-2-yl | H |
| 12 | H | (4-t-Butyl)-Phenoxy | H | H |
| 13 | Bromo | H | H | OMe |
| 14 | Bromo | H | H | OEt |
| 15 | 1-morpholino | H | H | NO2 |

TABLE 1-continued

| Compound number | 2 | 3 | 4 | 5 |
|---|---|---|---|---|
| 16 | 3-Trifluoromethyl-phenoxy | H | H | NO2 |
| 17 | methoxy | H | H | SMe |
| 18 | 4-Fluorobenzyloxy | H | H | SMe |
| 19 | 4-Methoxybenzyloxy | H | H | SMe |
| 20 | OH | H | H | SMe |
| 21 | OH | H | H | OMe |
| 22 | Allyloxy | H | H | SMe |
| 23 | Cyclopropyl methoxy | H | H | SMe |
| 24 | O-3-Pentyl | H | H | SMe |
| 25 | benzyloxy | H | H | OMe |
| 26 | Benzyloxy | H | H | SMe |
| 27 | H | 4-Fluorophenyl | H | H |
| 28 | H | 4-Chlorophenoxy | H | H |
| 29 | H | OMe | H | OMe |
| 30 | H | 4-Methoxyphenoxy | H | H |
| 31 | Fluoro | H | H | Trifluoromethyl |
| 32 | 4-ChloroPhenylthio | H | H | H |
| 33 | 3-Carboxybenzyloxy | H | H | SMe |
| 34 | 4-Carboxybenzyloxy | H | H | SMe |
| 35 | 3-Nitrobenzyloxy | H | H | SMe |
| 36 | 4-Isopropylbenzyloxy | H | H | SMe |
| 37 | 4-Methylsulphonyl-benzyloxy | H | H | SMe |
| 38 | 3,5-Difluorobenzyloxy | H | H | SMe |
| 39 | 4-Vinylbenzyloxy | H | H | SMe |
| 40 | 2,4-Difluorobenzyloxy | H | H | SMe |
| 41 | 3-Trifluoromethyl-4-fluorobenzyloxy | H | H | SMe |
| 42 | 3-Trifluoromethyl-benzyloxy | H | H | SMe |
| 43 | 3,4-Methylenedioxy-benzyloxy | H | H | SMe |
| 44 | 3-Fluorobenzyloxy | H | H | SMe |
| 45 | 2-Methylbenzyloxy | H | H | SMe |
| 46 | 3-Methylbenzyloxy | H | H | SMe |
| 47 | 2-Fluorobenzyloxy | H | H | SMe |
| 48 | 4-Bromobenzyloxy | H | H | SMe |
| 49 | 4-Methylbenzyloxy | H | H | SMe |
| 50 | 3-Methoxybenzyloxy | H | H | SMe |
| 51 | 3,4-Difluorobenzyloxy | H | H | SMe |
| 52 | 3-Carboxybenzyloxy | H | H | H |
| 53 | 3,5-Difluorobenzyloxy | H | H | H |
| 54 | 2-Cyanoobenzyloxy | H | H | H |
| 55 | 2-Methylbenzyloxy | H | H | H |
| 56 | 2,4-Difluorobenzyloxy | H | H | H |
| 57 | 3-Trifluoromethyl-benzyloxy | H | H | H |
| 58 | 2,5-Difluorobenzyloxy | H | H | H |
| 59 | 3,4-Methylenedioxy-benzyloxy | H | H | H |
| 60 | 3-Fluorobenzyloxy | H | H | H |
| 61 | 2-Fluorobenzyloxy | H | H | H |
| 62 | 4-Fluorobenzyloxy | H | H | H |
| 63 | 3-Methoxybenzyloxy | H | H | H |
| 64 | 3-Phenylallyloxy | H | H | SMe |
| 65 | 3-Phenylpropoxy | H | H | SMe |
| 66 | Cyclohexylmethoxy | H | H | SMe |
| 67 | 2-N-Methylpyrrolidino-2-Ethoxy | H | H | SMe |
| 68 | 2-(4-Bromophenoxy)-ethoxy | H | H | SMe |
| 69 | 2-Hydroxy-2-Trifluoromethyl-ethoxy | H | H | SMe |
| 70 | 4-(3,5-dimethylisoxozolo)-methoxy | H | H | SMe |
| 71 | 2-(2-1,3-diazolo)-ethoxy | H | H | SMe |
| 72 | 2-Carboxyfurano-methoxy | H | H | SMe |
| 73 | H | 2-Chlorobenzyloxy | H | H |
| 74 | Benzyloxy | H | H | 2-Methoxyethoxy |
| 75 | 2-Methylbenzyloxy | H | H | 2-Methoxyethoxy |

TABLE 1-continued

| Compound number | 2 | 3 | 4 | 5 |
|---|---|---|---|---|
| 76 | Benzyloxy | H | H | Trifluoromethoxy |
| 77 | 3-Methylbenzyloxy | H | H | Trifluoromethoxy |
| 78 | Hydroxy | H | H | t-Butyl |
| 79 | 3-(5-methyl)isoxazolomethoxy | H | H | SMe |
| 80 | 2-Furanomethoxy | H | H | SMe |
| 81 | 3-Pyridomethoxy | H | H | SMe |
| 82 | 2-Thiophenomethoxy | H | H | SMe |
| 83 | 3-Thiophenomethoxy | H | H | SMe |
| 84 | Benzyloxy | H | H | 2-Cyanobenzyloxy |
| 85 | 4-Phenylcarbamoyl-benzyloxy | H | H | SMe |
| 86 | 4-Carbamoylbenzyloxy | H | H | SMe |
| 87 | 4-benzoylbenzyloxy | H | H | SMe |
| 88 | 4-Sulphamoyl-benzyloxy | H | H | SMe |
| 89 | 4-Carboxymethyl-benzyloxy | H | H | SMe |
| 90 | 4-(2-Methylcarboxy)-phenylbenzyloxy | H | H | SMe |
| 91 | 4-Carboxymethoxy-benzyloxy | H | H | SMe |
| 92 | 4-Cyanobenzyloxy | H | H | SMe |
| 93 | 4-Nitrobenzyloxy | H | H | SMe |
| 94 | H | 2-Cyanobenzyloxy | H | 2-Cyanobenzyloxy |
| 95 | H | 2-Fluorobenzyloxy | H | 2-Fluorobenzyloxy |
| 96 | H | 2-Chlorobenzyloxy | H | 2-Chlorobenzyloxy |
| 97 | H | 3-(5-methyl)isoxazolylmethoxy | H | 3-(5-methyl)-isoxazolylmethoxy |
| 98 | H | 2-[2-methylthiazol-4-yl]ethoxy | H | 2-[4-(2-methyl)-thiazolyl]-ethoxy |
| 99 | H | Benzyloxy | H | 2-Fluorobenzyloxy |
| 100 | H | 2-chlorobenzyloxy | H | 2-Fluorobenzyloxy |
| 101 | H | 2-Methylbenzyloxy | H | 2-Fluorobenzyloxy |
| 102 | H | 2-Cyanobenzyloxy | H | 2-Fluorobenzyloxy |
| 103 | H | 2-Trifluoromethyl-benzyloxy | H | 2-Fluorobenzyloxy |
| 104 | H | 2-Trifluoromethoxy-benzyloxy | H | 2-Fluorobenzyloxy |
| 105 | H | 2-Methoxybenzyloxy | H | 2-Fluorobenzyloxy |
| 106 | H | 2-[2-methylthiazol-4-yl]ethoxy | H | Isopropoxy |
| 107 | H | 2-[2-methylthiazol-4-yl]ethoxy | H | 2-Pyridylmethoxy |
| 108 | H | 5-methylisoxazol-3-yl-methoxy | H | Isopropoxy |
| 109 | H | 5-methylisoxazol-3-yl-methoxy | H | 2-Methylbenzyloxy |
| 110 | H | 5-methylisoxazol-3-yl-methoxy | H | 4-(2-methyl)-thiazolylmethoxy |
| 111 | H | 2-[4-methylthiazol-5-yl]ethoxy | H | 2-Methylbenzyloxy |
| 112 | H | 2-[4-methylthiazol-5-yl]-ethoxy | H | 3-(5-methyl)-isoxazolylmethoxy |
| 113 | 4-Isopropylbenzyloxy | H | H | Methylsulphoxy |
| 114 | Benzyloxy | H | H | Methylsulphonyl |
| 115 | Ethylthio | Methoxy | H | H |
| 116 | Hydroxy | H | H | Methylthio |
| 117 | H | 2-chlorobenzyloxy | H | H |
| 118 | H | 2-[4-methylthiazol-5-yl]-ethoxy | H | Isopropoxy |
| 119 | H | 2-[4-methylthiazol-5-yl]-ethoxy | H | 2-Pyridylmethoxy |
| 120 | H | 5-methylisoxazol-3-yl-methoxy | H | Isopropoxy |
| 121 | H | 5-methylisoxazol-3-yl-methoxy | H | 2-Methylbenzyloxy |
| 122 | H | 5-methylisoxazol-3-yl-methoxy | H | 2-[4-(2-methyl)-thiazolyl]-ethoxy |
| 123 | H | 2-[4-methylthiazol-5-yl]-ethoxy | H | 2-Methylbenzyloxy |
| 124 | Benzyloxy | H | H | Methylthio |
| 125 | Benzyloxy | H | H | Methylthio |

TABLE 1-continued

| Compound number | 2 | 3 | 4 | 5 |
|---|---|---|---|---|
| 126 | Benzyloxy | H | H | Bromo |
| 127 | Benzyloxy | H | H | Methylthio |

TABLE 2

| Compound Number | Parent Molecular Weight | Mass Spec (+ve/−ve) | Synthetic scheme |
|---|---|---|---|
| 1 | 271.34 | 272, | 1 |
| 2 | 317.35 | 318, | 1 |
| 3 | 361.25 | 362, | 1 |
| 4 | 331.37 | 332, | 1 |
| 5 | 399.04 | 398, 400, 402, | 1 |
| 6 | 412.85 | 411, 413 | 1 |
| 7 | 392.44 | 391, 393 | 1 |
| 8 | 303.75 | 302, 304 | 1 |
| 9 | 294.14 | 295, 293 | 1 |
| 10 | 327.69 | 326, 328 | 1 |
| 11 | 364.47 | 365, 363 | 1 |
| 12 | 373.46 | 374, 372 | 1 |
| 13 | 334.17 | 334, 336 | 1 |
| 14 | 348.2 | 348, 350 | 1 |
| 15 | 355.35 | 354, 356 | 1 |
| 16 | 430.34 | 431, | 1 |
| 17 | 301.37 | 302, 300 | 2 |
| 18 | 395.46 | 396, 394 | 2 |
| 19 | 407.49 | 408, 406 | 2 |
| 20 | 287.34 | 288, 286 | 2 |
| 21 | 271.28 | 272, 270 | 2 |
| 22 | 327.41 | 328, | 2 |
| 23 | 341.43 | 342, | 2 |
| 24 | 357.48 | 358, | 2 |
| 25 | 361.4 | 362, 360 | 2 |
| 26 | 377.47 | 378, 376 | 2 |
| 27 | 319.34 | 320, 318 | 2 |
| 28 | 351.79 | 352, 350 | 2 |
| 29 | 285.3 | 286, 284 | 2 |
| 30 | 347.37 | 348, 346 | 2 |
| 31 | 311.24 | 312, 310 | 2 |
| 32 | 367.86 | 368, 366 | 2 |
| 33 | 421.48 | 422, | 2 |
| 34 | 421.48 | 422, 420 | 2 |
| 35 | 422.46 | 423, 421 | 2 |
| 36 | 419.55 | 420, 418 | 2 |
| 37 | 455.56 | 456, 454 | 2 |
| 38 | 413.45 | 414, 412 | 2 |
| 39 | 403.5 | 404, 402 | 2 |
| 40 | 413.45 | 414, 412 | 2 |
| 41 | 463.45 | 464, 462 | 2 |
| 42 | 445.46 | 446, 444 | 2 |
| 43 | 421.48 | 422, 420 | 2 |
| 44 | 395.46 | 396, 394 | 2 |
| 45 | 391.49 | 392, 390 | 2 |
| 46 | 391.49 | 392, 390 | 2 |
| 47 | 395.46 | 396, 394 | 2 |
| 48 | 456.36 | 456, 458, 454, 456 | 2 |
| 49 | 391.49 | 392, 390 | 2 |
| 50 | 407.49 | 408, 406 | 2 |
| 51 | 413.45 | 414, 412 | 2 |
| 52 | 375.38 | 376, 374 | 2 |
| 53 | 367.36 | 368, 366 | 2 |
| 54 | 356.38 | 357, 355 | 2 |
| 55 | 345.4 | 346, 344 | 2 |
| 56 | 367.36 | 368, 366 | 2 |
| 57 | 399.37 | 400, 398 | 2 |
| 58 | 367.36 | 368, 366 | 2 |
| 59 | 375.38 | 376, 374 | 2 |
| 60 | 349.36 | 350, 348 | 2 |
| 61 | 349.36 | 350, 348 | 2 |
| 62 | 349.36 | 350, 348 | 2 |
| 63 | 361.4 | 362, 360 | 2 |
| 64 | 403.5 | 404, 402 | 2 |
| 65 | 405.52 | 406, 404 | 2 |
| 66 | 383.51 | 384, 382 | 2 |
| 67 | 398.53 | 399, 397 | 2 |
| 68 | 486.39 | 486, 488, 484, 486 | 2 |
| 69 | 399.39 | 400, 398 | 2 |
| 70 | 396.47 | 397, 395 | 2 |
| 71 | 387.46 | 388, 386 | 2 |
| 72 | 411.44 | 412, 410 | 2 |
| 73 | 365.82 | 366, | 2 |
| 74 | 405.45 | 406 | 2 |
| 75 | 419.48 | 420 | 2 |
| 76 | 415.37 | 416 | 2 |
| 77 | 429.4 | 430 | 2 |
| 78 | 297.36 | 298, 296 | 2 |
| 79 | 382.44 | 383, | 2 |
| 80 | 367.43 | 368, | 2 |
| 81 | 378.45 | 379, | 2 |
| 82 | 383.49 | 384, | 2 |
| 83 | 383.49 | 384, | 2 |
| 84 | 462.51 | 463 | 2 |
| 85 | 496.59 | 497 | 2 |
| 86 | 420.49 | 421 | 2 |
| 87 | 481.57 | 482 | 2 |
| 88 | 456.54 | 457 | 2 |
| 89 | 435.5 | 436 | 2 |
| 90 | 511.6 | 512 | 2 |
| 91 | 451.5 | 452 | 2 |
| 92 | 402.48 | 403 | 2 |
| 93 | 422.46 | 423 | 2 |
| 94 | 487.52 | 488 | 2 |
| 95 | 473.48 | 474, | 2 |
| 96 | 506.39 | 506, | 2 |
| 97 | 447.45 | 448, 446 | 2 |
| 98 | 507.63 | 508, | 2 |
| 99 | 455.49 | 456, 454 | 3 |
| 100 | 489.94 | 490, 492, 488, 490 | 3 |
| 101 | 469.52 | 470, 68 | 3 |
| 102 | 480.5 | 481, 479 | 3 |
| 103 | 523.49 | 524, 522 | 3 |
| 104 | 539.49 | 540, 538 | 3 |
| 105 | 485.52 | 486, 484 | 3 |
| 106 | 424.52 | 425, 423 | 3 |
| 107 | 473.55 | 474, 472 | 3 |
| 108 | 394.43 | 395, 393 | 3 |
| 109 | 456.5 | 457, 455 | 3 |
| 110 | 463.52 | 464, 462 | 3 |
| 111 | 486.59 | 487, 485 | 3 |
| 112 | 477.54 | 478, 476 | 3 |
| 113 | 435.55 | 434, 436 | 5 |
| 114 | 409.464 | , 408 | 5 |
| 115 | 329.42 | 330, | 1 |
| 116 | 301.37 | 302, 300 | 2 |
| 117 | 379.85 | 380, | 2 |
| 118 | 438.55 | 439, | 3 |
| 119 | 487.58 | 488, | 3 |
| 120 | 408.46 | 409, | 3 |
| 121 | 470.53 | 471, 469 | 3 |
| 122 | 477.54 | 478, 476 | 3 |
| 123 | 500.62 | 501, 499 | 3 |
| 124 | 454.57 | 455.13 | 4 |
| 125 | 406.51 | 407.12 | 4 |
| 126 | 453.339 | 453, | 4 |
| 127 | 420.534 | 421, | 4 |

EXAMPLE K

Scheme 5: Preparation of 6-(E-2-[-2-(2-benzyloxy)-5-methylsulfanyl-phenyl]-vinyl)-nicotinic Acid, N-methoxyamide,

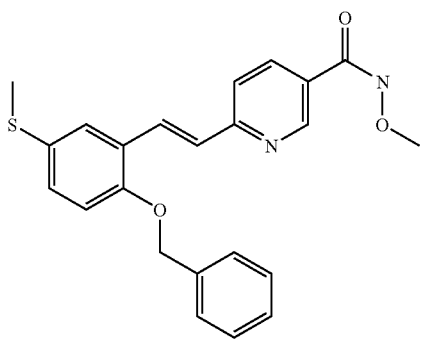

To a stirred suspension of 6-{(E)-2-[2-(benzyloxy)-5-(methylthio)phenyl]ethenyl}nicotinic acid (82 mg, 0.22 mmol) in DCM (10 ml) was added oxalyl chloride (35 mg, 0.28 mmol) and DMF (catalytic amount). The mixture was stirred at ambient temperature for 17 hours, and volatile material removed by evaporation to give a gum which was then suspended in DCM (10 ml). Methoxyamine hydrochloride (37 mg, 0.44 mmol) and triethylamine (0.06 ml, 0.43 mmol) were added to the suspension and the resulting solution stirred at ambient temperature for 4 hours. It was then diluted with DCM (20 ml) and washed sequentially with 2 M hydrochloric acid (20 ml), brine (20 ml), and dried over MgSO$_4$. Volatile material was removed by evaporation to leave a gum which was purified by flash chromatography on silica, eluting with 1–2% methanol in DCM to give an oil. Triturated with diethyl ether gave 6-(E-2-[-2-(2-benzyloxy)-5-methylsulfanyl-phenyl]-vinyl)-nicotinic acid, N-methoxyamide (33 mg) as a solid, NMR: $\delta_H$ (300 MHZ, DMSO-d$_6$) 2.48 (s, 3 H+DMSO), 3.72 (s, 3 H), 5.22 (s, 2 H), 7.11 (d, 1 H), 7.24 (s, 1 H), 7.30–7.53 (m, 7 H), 7.68 (s, 1 H), 8.05 (m, 2 H), 8.88 (s, 1 H), 11.82 (s, 1 H); m/z 407 (M+H)$^+$.

EXAMPLE L

Scheme 6: Preparation of 6-(E-2-[-2-(3,5-dibenzyloxy)-phenyl]-vinyl)-pyridine-3-oxyacetic acid.

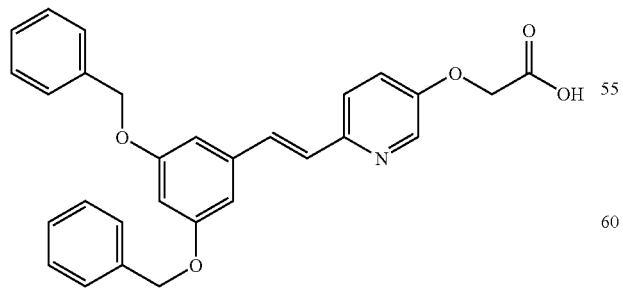

To a stirred solution of 6-(E-2-[-2-(3,5-dibenzyloxy)-phenyl]-vinyl)-pyridine-3-oxyacetic acid t-butyl ester (100 mg, 0.19 mmol) in dichloromethane (2 ml) was added trifluoroacetic acid (1 ml). The solution was stirred at ambient temperature for 6 hours. Volatile material was removed by evaporation, and the residue azeotroped with toluene to give an oil. This was triturated under diethyl ether to give the title compound (72 mg) as a solid, NMR: $\delta_H$ (300 MHz, DMSO-d$_6$) 4.80 (s, 2 H), 5.12 (s, 4 H), 6.60 (s, 1 H), 6.89 (s, 2 H), 7.08–7.60 (m, 14 H), 8.31 (s, 1 H), m/z 468 (M+H)$^+$.

The requisite t-butyl ester starting material was prepared as follows:

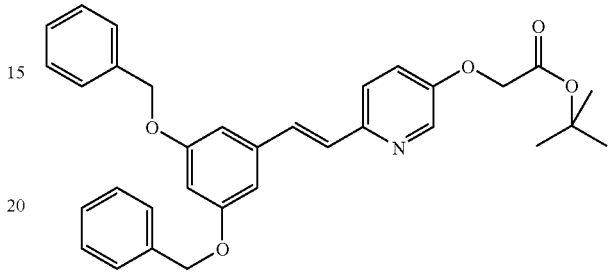

To a suspension of 3-hydroxy-6-(E-2-[-2-(3,5-dibenzyloxy)-phenyl]-vinyl) pyridine (150 mg) in anhydrous THF (10 ml) was added sodium hydride (30 mg) at ambient temperature, under an atmosphere of nitrogen. The reaction was allowed to stir for 20 minutes and then t-butyl bromo acetate (0.06 ml) was added. The reaction was stirred for 30 minutes before being cooled to 0° C. and DMF (3 ml) added. The reaction was then allowed to warm ambient temperature, when water (20 ml) was added. The aqueous was extracted with ethyl acetate (3×20 ml) and the extracts combined, dried (MgSO$_4$) and evaporated to leave an oil. This was purified by flash chromatography on a 10 g silica Bondelut, to give an oil which was triturated under diethyl ether: hexane (1:1) to give 6-(E-2-[-2-(3,5-dibenzyloxy)-phenyl]-vinyl)-pyridine-3-oxyacetic acid t-butyl ester (135 mg) as a solid, MS m/z 524 (M+H)$^+$.

The requisite 3-hydroxy pyridine starting material was prepared as follows:

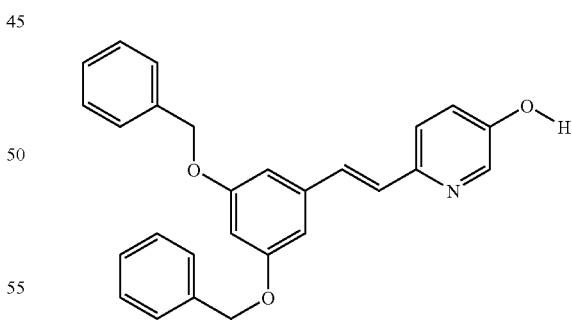

To a suspension of 3-acetoxy-6-(E-2-[-2-(3,5-dibenzyloxy)-phenyl]-vinyl pyridine (100 mg) in methanol (2 ml) was added sodium hydroxide (0.44 ml, 0.86 mmol), and the mixture stirred at ambient temperature for 1.5 hours. An excess of 2 M hydrochloric acid was added. A precipitate formed, which was filtered off, washed sequentially with water and ether, and dried under vacuum at 60° C. for 5 hours, to give 3-hydroxy-6-(E-2-[-2-(3,5-dibenzyloxy)-phenyl]-vinyl) pyridine (82 mg) as a solid, m/z 410 (M+H)$^+$.

The requisite 3-acetoxy pyridine starting material was prepared as follows:

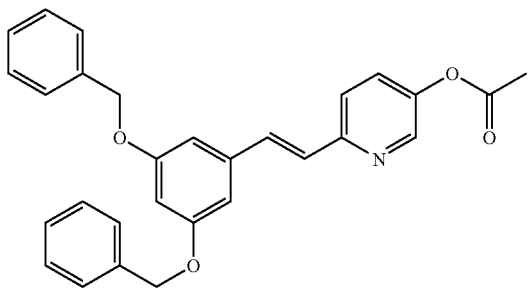

To a stirred solution of 6-{2-[3,5-bis(benzyloxy)phenyl]-2-hydroxyethyl}pyridin-3-ol (105 mg) in acetic anhydride (0.23 ml) was added acetic acid (0.23 ml); the mixture was heated to 120° C. and stirred for 17 hours. It was then allowed to cool to ambient temperature and water (10 ml) was added, followed by extraction with ethyl acetate (3×30 ml). The extracts were combined, dried (MgSO$_4$) and evaporated to give an oil, which was triturated under hexane to give the title compound (80 mg) as a solid. MS ES$^+$ 452 (M+H)$^+$.

The requisite 6-{2-[3,5-bis(benzyloxy)phenyl]-2-hydroxyethyl}pyridin-3-ol starting material was prepared as follows:

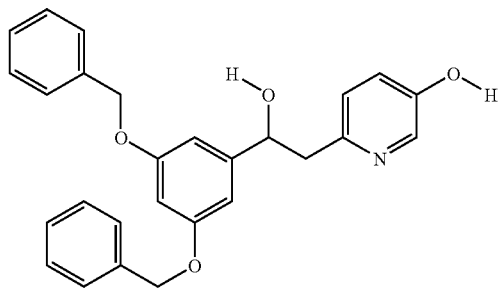

To a stirred solution of 5-{[tert-butyl(dimethyl)silyl]oxy}-2-methyl pyridine (1.20 g) in anhydrous THF (15 ml) under nitrogen and at −78° C. was added LDA (3.22 ml), and the solution stirred at −78° C. for 1 hour. 3,5 dibenzyloxy-benzaldehyde (2.05 g) was then added dropwise as a solution in THF, and the reaction mixture allowed to warm to ambient temperature over 1 hour. Water (20 ml) was added and the resulting mixture extracted with ethyl acetate (3×30 ml). The extracts were combined, washed with brine (20 ml), dried (MgSO$_4$) and evaporated to give a gum. This was dissolved in THF (10 ml) and concentrated hydrochloric acid (10 ml) added. The mixture was stirred at ambient temperature for 3 hours, cooled to 0° C. and taken to pH 8.5 with concentrated ammonia solution. The mixture was diluted with water (50 ml) and extracted with ethyl acetate (3×100 ml). The extracts were combined, dried (MgSO$_4$) and evaporated to leave an oil which was purified by MPLC on silica, eluting with 60–100% ethyl acetate in hexane to give 6-{2-[3,5-bis(benzyloxy)phenyl]-2-hydroxyethyl}pyridin-3-ol (2.25 g) as a glass, m/z 428 (M+H)$^+$.

EXAMPLE M

Scheme 7: Preparation of E 2-{-2-[3,5-di-(2-chlorobenzyloxy)]-phenyl}-vinyl-thiazole-4-carboxylic Acid

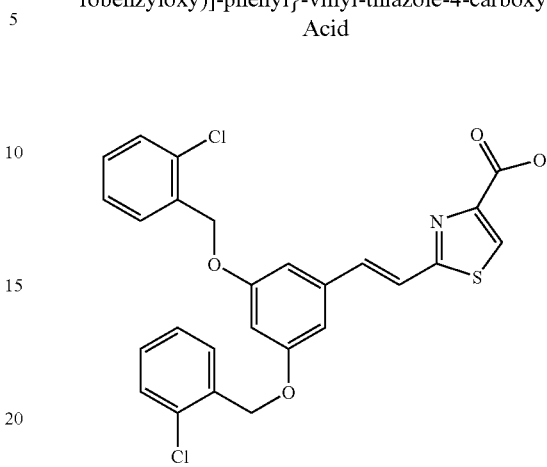

This was prepared from E 2-{-2-[3,5-di-(2-chlorobenzyloxy)]-phenyl}-vinyl-thiazole-4-carboxylic acid ethyl ester by alkaline hydrolysis in a manner similar to that described in Example A, Scheme 1.

The requisite ethyl ester starting material was prepared as follows:

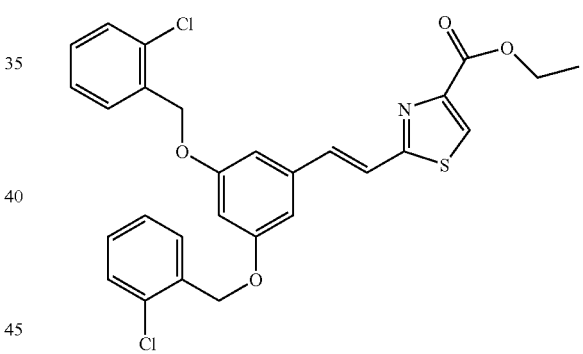

Ethyl 2-[(diethoxyphophoryl)methyl]-1,3-thiazole-4-carboxylate (280 mgs, 0.91 mmol) in dry tetrahydrofuran (10 ml) was added to a stirred suspension of sodium hydride (40 mgs of 60% dispersion, 1 mmol) in dry tetrahydrofuran (10 ml). After stirring for half an hour at room temperature a solution of 3,5 bis (2-chlorobenzyl)benazaldehyde (420 mgs 1.09 mmol) in dry tetrahydrofuran (10 ml) was added slowly. The mixture was stirred at ambient temperature for 4 hours, quenched with water and acidified with 2 M aq hydrochloric acid. The mixture was extracted with ethyl acetate and the extrac combined, dried (MgSO$_4$) and evaporated to leave a gum. Chromatography on silica, eluting with 20% EtOAc in hexane, gave E 2-{-2-[3,5-di-(2-chlorobenzyloxy)]-phenyl}-vinyl-thiazole-4-carboxylic acid ethyl ester (260 mgs), NMR $\delta_H$ (300 MHz, DMSO-d$_6$); 1.25–1.35 (3 H,t); 4.25–4.35 (2 H, q); 5.2 (4 H, s); 6.69 (1 H, s); 7.08 (2 H,s); 7.34–7.45 (4 H, m); 7.45–7.55 (3 H,m); 7.55–7.65 (3 H,m); 8.45 (1 H, m).

The requisite ethyl 2-[(diethoxyphophoryl)methyl]-1,3-thiazole-4-carboxylate starting material was prepared as follows:

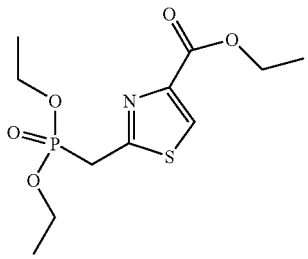

Ethyl 2-(bromomethyl)-1,3-thiazole-5-carboxylate (460 mgs, 1.85 mmol) in dry tetrahydrofuran (2.5 ml) was added dropwise to triethylphosphite (2.5 ml, 2.46 g, 14.8 mmol) under argon at a temperature of 105° C. On completion of the addition the mixture was warmed to 140° C. at which it was maintained for one hour. The triethylphosphite was then removed under reduced pressure and the resultant material chromatographed (silica, EtOAc/hexane) to give ethyl 2-[(diethoxyphophoryl)methyl]-1,3-thiazole-4-carboxylate (300 mgs), NMR: $\delta_H$ (300 MHz, DMSO-$d_6$): 1,15–1.35 (9 H, m); 3.95–4.12 (4 H, m); 4.22–4.35 (2 H,q); 8.43 (1 H,s).

The requisite ethyl 2-(bromomethyl)-1,3-thiazole-5-carboxylate starting material was prepared as follows:

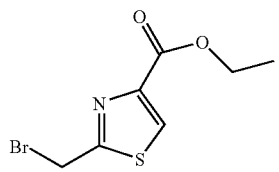

N-Bromosuccinimide (0.91 g, 5.1 mmol) was added to a solution of ethyl 2-methyl-thiazole-5-carboxylate (0.8 g, 4.7 mmol) in carbon tetrachloride. The resultant reaction mixture was stirred for one hour whilst being illuminated by a photoflood lamp. After removing the solvent from the reaction mixture the resultant material was partitioned between ethyl acetate and water. The organic phase was then separated off, dried (MgSO$_4$) and the evaporated. Chromatography on silica, eluting with 30% ethyl acetate in hexane, gave ethyl 2-(bromomethyl)-1,3-thiazole-5-carboxylate (490 mgs), NMR: $\delta_H$ (300 MHz, DMSO-$d_6$, 1.20–1.38 (3 H,t); 4.20–4.37 (2 H,q); 5.05 (2 H, s); 8.55 (1 H, s).

EXAMPLE N

By analogous methods to those described compounds N$_{1-8}$ in Table 3 were also made.

TABLE 2

| No | Structure | Route (Example) | MS | NMR |
|----|-----------|-----------------|-----|-----|
| 1 | E FORM | I | 455 | $\delta_H$(300MHz, CDCl$_3$) 2.48 (s, 3H), 3.43 (s, 3H), 5.20 (s, 2H), 6.92 (d, 1H), 7.25 (s, CHCl$_3$+1H), 7.33–7.48 (m, 7H), 7.57 (d, 1H), 7.60 (s, 1H), 8.13 (d, 1H), 8.32 (d, 1H), 9.26 (s, 1H). |
| 2 | E FORM | K Scheme 5 | 407 | $\delta_H$(300MHz, DMSO-$d_6$) 2.48 (s, 3H+DMSO), 3.72 (s, 3H), 5.22 (s, 2H), 7.11 (d, 1H), 7.24 (s, 1H), 7.30–7.53 (m, 7H), 7.68 (s, 1H), 8.05 (m, 2H), 8.88 (s, 1H), 11.82 (s, 1H). |

TABLE 2-continued
| No | Structure | Route (Example) | MS | NMR |
|---|---|---|---|---|
| 3 | 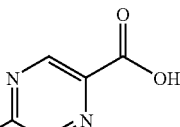 E FORM | A Scheme 1 | 373 | δ_H(300MHz, DMSO-d_6) 1.2 (s, 9H), 7.0 (d, 3H), 7.4 (m, 6H), 7.8 (d, 1H), 8.7 (s,1H), 9.1 (s,1H). |
| 4 | 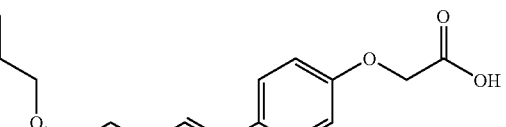 E FORM | L Scheme 6 | 468 | δ_H(300MHz, DMSO-d_6) 4.80 (s, 2H), 5.12 (s, 4H), 6.60 (s, 1H), 6.89 (s, 2H), 7.08–7.60 (m, 14H), 8.31 (s, 1H). |
| 5 | 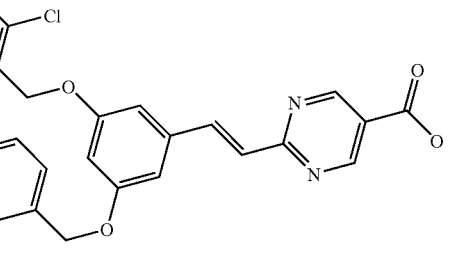 E FORM | A Scheme 1* | | δ_H(300MHz, DMSO-d_6) 5.21 (4H, s), 6.72 (1H, s), 7.10 (2H, app s), 7.30–7.44 (5H, m), 7.44–7.55 (2H, m), 7.55–7.65 (2, m), 7.90–8.1 (1H, d), 9.14 (2H, s). |
| 6 | 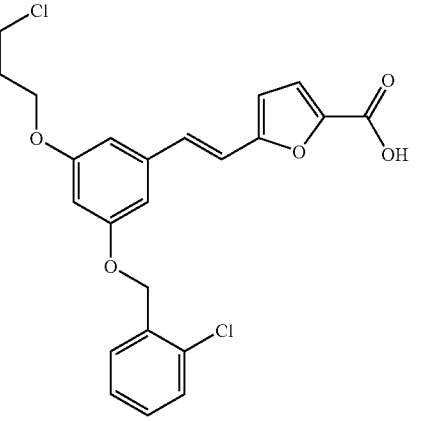 E FORM | M Scheme 7 (by analogy with Example 8) | | δ_H(300MHz, DMSO-d_6) 5.20 (4H, s), 6.62 (1H, s), 6.71 (1H, d), 6.97 (2H, d), 7.14 (1H, d), 7.26 (2H, m), 7.40 (4H, m), 7.52 (2H, m), 7.63 (2H, m). |

TABLE 2-continued

| No | Structure | Route (Example) | MS | NMR |
|---|---|---|---|---|
| 7 | 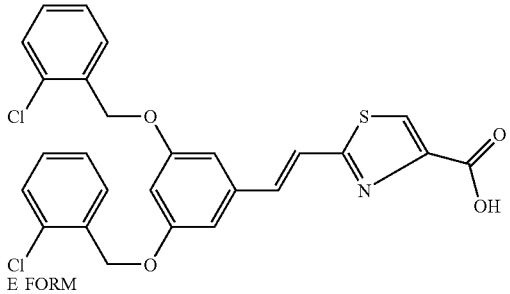 E FORM | M Scheme 7 (by analogy with Example 8) | 512 514 | δ$_H$(300MHz, DMSO-d$_6$), 5.19 (4H, s), 6.68 (1H, s), 7.01 (2H, s), 7.31–7.45 (5, m), 7.45–7.58 (~2.5H, m), 7.58–7.69 (~2.5H, m), 7.87 (1H, s) |
| 8 | 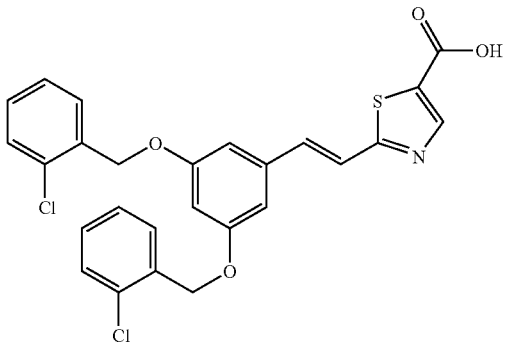 | M Scheme 7 ** (described) | 512 | δ$_H$(300MHz, DMSO-d$_6$), 5.19 (4H, s), 6.72 (1H, s), 7.08 (2H, s), 7.30–7.45 (4H, m), 7.45–7.55 (2H, m), 7.55–7.68 (4H, m), 8.33 (1H, s) |

*Example 5 - starting material (ethyl 2-methyl pyrimidine-5-carboxylate) prepared according to J Het Chem 27 295 (1990).
**Ethyl 2 methyl-1,3-thiazole-5-carboxylate prepared as described in J. Am. Chem. Soc. 1982, 104, 4461–4465

The compounds A–I, J$_{1-127}$, K, L, M and N$_{1-8}$ were found to have an activity of at least 40% activity at 10 μm when tested in the GLK/GLKRP scintillation proximity assay described below.

BIOLOGICAL

Tests

The biological effects of the compounds of the invention may be tested in the following way:

(1) Enzymatic activity of GLK may be measured by incubating GLK, ATP and glucose. The rate of product formulation may be determined by coupling the assay to a G-6-P dehydrogenase, NADP/NADPH system and measuring the increase in optical density at 340 nm (Matschinsky et al 1993).

(2) A GLK/GLKRP binding assay for measuring the binding interactions between GLK and GLKRP. The method may be used to identify compounds which modulate GLK by modulating the interaction between GLK and GLKRP. GLKRP and GLK are incubated with an inhibitory concentration of F-6-P, optionally in the presence of test compound, and the extent of interaction between GLK and GLKRP is measured. Compounds which either displace F-6-P or in some other way reduce the GLK/GLKRP interaction will be detected by a decrease in the amount of GLK/GLKRP complex formed. Compounds which promote F-6-P binding or in some other way enhance the GLK/GLKRP interaction will be detected by an increase in the amount of GLK/GLKRP complex formed. A specific example of such a binding assay is described below

GLK/GLKRP SCINTILLATION PROXIMITY ASSAY

Recombinant human GLK and GLKRP were used to develop a "mix and measure" 96 well SPA (scintillation proximity assay). (A schematic representation of the assay is given in FIG. 3). GLK (Biotinylated) and GLKRP are incubated with streptavidin linked SPA beads (Amersham) in the presence of an inhibitory concentration of radiolabelled [3H]F-6-P (Amersham Custom Synthesis TRQ8689), giving a signal as depicted in FIG. 3. Compounds which either displace the F-6-P or in some other way disrupt the GLK/GLKRP binding interaction will cause this signal to be lost.

Binding assays were performed at room temperature for 2 hours. The reaction mixtures contained 50 mM Tris-HCl (pH=7.5) 2 mM ATP, 5 mM MgCl$_2$, 0.5 mM DTT, recombinant biotinylated GLK (0.1 mg), recombinant GLKRP (0.1 mg), 0.05 mCi [3H] F-6-P (Amersham) to give a final volume of 100 ml. Following incubation, the extent of GLK/GLKRP complex formation was determined by addition of 0.1 mg/well avidin linked SPA beads (Amersham) and scintillation counting on a Packard TopCount NXT.

The exemplified compounds described above were found to have an activity of at least 40% activity at 10 μm when tested in the GLK/GLKRP scintillation proximity assay.

(3) A F-6-P/GLKRP binding assay for measuring the binding interaction between GLKRP and F-6-P. This method may be used to provide further information on the mechanism of action of the compounds. Compounds identified in the GLK/GLKRP binding assay may modulate the interaction of GLK and GLKRP either by displacing F-6-P or by modifying the GLK/GLKRP interaction in some other way.

For example, protein—protein interactions are generally known to occur by interactions through multiple binding sites. It is thus possible that a compound which modifies the interaction between GLK and GLKRP could act by binding to one or more of several different binding sites.

The F-6-P/GLKRP binding assay identifies only those compounds which modulate the interaction of GLK and GLKRP by displacing F-6-P from its binding site on GLKRP.

GLKRP is incubated with test compound and an inhibitory concentration of F-6-P, in the absence of GLK, and the extent of interaction between F-6-P and GLKRP is measured. Compounds which displace the binding of F-6-P to GLKRP may be detected by a change in the amount of GLKRP/F-6-P complex formed. A specific example of such a binding assay is described below

F-6-P/GLKRP SCINTILLATION PROXIMITY ASSAY

Recombinant human GLKRP was used to develop a "mix and measure" 96 well scintillation proximity assay. (A schematic representation of the assay is given in FIG. 4). FLAG-tagged GLKRP is incubated with protein A coated SPA beads (Amersham) and an anti-FLAG antibody in the presence of an inhibitory concentration of radiolabelled [3H]F-6-P. A signal is generated as depicted in FIG. 4. Compounds which displace the F-6-P will cause this signal to be lost. A combination of this assay and the GLK/GLKRP binding assay will allow the observer to identify compounds which disrupt the GLK/GLKRP binding interaction by displacing F-6-P.

Binding assays were performed at room temperature for 2 hours. The reaction mixtures contained 50 mM Tris-HCl (pH=7.5), 2 mM, ATP, 5 mM $MgCl_2$, 0.5 mM DTT, recombinant FLAG tagged GLKRP (0.1 mg), Anti-Flag M2 Antibody (0.2 mg) (IBI Kodak), 0.05 mCi [3H] F-6-P (Amersham) to give a final volume of 100 ml. Following incubation, the extent of F-6-P (Amersham) complex formation was determined by addition of 0.1 mg/well protein A linked SPA beads (Amersham) and scintillation counting on a Packard TopCount NXT.

PRODUCTION OF RECOMBINANT GLK AND GLKRP

Preparation of mRNA

Human liver total mRNA was prepared by polytron homogenisation in 4 M guanidine isothiocyanate, 2.5 mM citrate, 0.5% Sarkosyl, 100 mM b-mercaptoethanol, followed by centrifugation through 5.7 M CsCl, 2.5 mM sodium acetate at 135,000 g (max) as described in Sambrook J, Fritsch E F & Maniatis T, 1989.

Poly $A^+$ mRNA was prepared directly using a Fast-Track™ mRNA isolation kit (Invitrogen).

PCR Amplification of GLK and GLKRP cDNA Sequences

Human GLK and GLKRP cDNA was obtained by PCR from human hepatic mRNA using established techniques described in Sambrook Fritsch & Maniatis, 1989. PCR primers were designed according to the GLK and GLKRP cDNA sequences shown in Tanizawa et al 1991 and Bonthron, D. T. et al 1994 (later corrected in Warner, J. P. 1995).

CLONING IN BLUESCRIPT II VECTORS

GLK and GLKRP cDNA was cloned in *E. coli* using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

TRANSFORMATIONS

*E. Coli* transformations were generally carried out by electroporation. 400 ml cultures of strains DH5a or BL21 (DE3) were grown in L-broth to an OD 600 of 0.5 and harvested by centrifugation at 2,000 g. The cells were washed twice in ice-cold deionised water, resuspended in 1 ml 10% glycerol and stored in aliquots at –70° C. Ligation mixes were desalted using Millipore V series™ membranes (0.0025 mm) pore size). 40 ml of cells were incubated with 1 ml of ligation mix or plasmid DNA on ice for 10 minutes in 0.2 cm electroporation cuvettes, and then pulsed using a Gene Pulser™ apparatus (BioRad) at 0.5 $kVcm^{-1}$, 250 mF, 250 ?. Transformants were selected on L-agar supplemented with tetracyline at 10 mg/ml or ampicillin at 100 mg/ml.

EXPRESSION

GLK was expressed from the vector pTB375NBSE in *E. coli* BL21 cells, producing a recombinant protein containing a 6-His tag immediately adjacent to the N-terminal methionine. Alternatively, another suitable vector is pET21(+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in *E. coli* BL21 cells, producing a recombinant protein containing a C-terminal FLAG tag. The protein was purified initially be DEAE Sepharose ion exchange followed by utilisation of the FLAG tag for final purification on an M2 anti-FLAG immunoaffinity column purchased from Sigma-Aldrich (cat no. A1205).

BIOTINYLATION OF GLK

GLK was biotinylated by reaction with biotinamidocaproate N-hydroxysuccinimide ester (biotin-NHS) purchased from Sigma-Aldrich (cat no. B2643). Briefly, free amino groups of the target protein (GLK) are reacted with biotin-NHS at a defined molar ratio forming stable amide bonds resulting in a product containing covalently bound biotin. Excess, non-conjugated biotin-NHS is removed from the product by dialysis. Specifically, 7.5 mg of GLK was added to 0.31 mg of biotin-NHS in 4 mL of 25 mM HEPES pH=7.3, 0.15 M KCl, 1 mM dithiothreitol, 1 mM EDTA, 1 mM $MgCl_2$ (buffer A). This reaction mixture was dialysed against 100 mL of buffer A containing a further 22 mg of biotin-NHS. After 4 hours excess biotin-NHS was removed by extensive dialysis against buffer A.

PHARMACEUTICAL COMPOSITIONS

The following illustrative representative pharmaceutical dosage forms of the invention as defined herein (the active ingredient being termed "Compound X"), for therapeutic or prophylactic use in humans:

|  | mg/tablet |
| --- | --- |
| (a) Tablet I | |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

|  | mg/capsule |
| --- | --- |
| (d) Capsule | |
| Compound X | 10 |
| Lactose Ph. Eur | 488.5 |
| Magnesium | 1.5 |

|  | (50 mg/ml) |
| --- | --- |
| (e) Injection I | |
| Compound X | 5.0% w/v |
| 1 M Sodium hydroxide solution | 15.0% v/v |
| 0.1 M Hydrochloric acid | |
| (to adjust pH = to 7.6) | |
| Polyethylene glycol 400 | 4.5% w/v |
| Water for injection to 100% | |

|  | (10 mg/ml) |
| --- | --- |
| (f) Injection II | |
| Compound X | 1.0% w/v |
| Sodium phosphate BP | 3.6% w/v |
| 0.1 M Sodium hydroxide solution | 15.0% v/v |
| Water for injection to 100% | |

|  | 1 mg/ml, buffered to pH = 6 |
| --- | --- |
| (g) Injection III | |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

|  | mg/ml |
| --- | --- |
| (h) Aerosol I | |
| Compound X | 10.0 |
| Sorbitan trioleate | 13.5 |
| Trichlorofluoromethane | 910.0 |
| Dichlorodifluoromethane | 490.0 |
| (i) Aerosol II | |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

|  | ml |
| --- | --- |
| (l) Ointment | |
| Compound X | 40 mg |
| Ethanol | 300 μl |
| Water | 300 μl |
| 1-Dodecylazacycloheptan-2-one | 50 μl |
| Propylene glycol | to 1 ml |

NOTE

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

REFERENCES

1 Printz, R. L., Magnuson, M. A. and Granner, D. K. (1993) Annual Review of Nutrition 13, 463–96
2 DeFronzo, R. A. (1988) Diabetes 37, 667–87
3 Froguel, P., Zouali, H., Vionnet, N., Velho, G., Vaxillaire, M., Sun, F., Lesage, S., Stoffel, M., Takeda J. and Passa, P. (1993) New England Journal of Medicine 328, 697–702
4 Bell, G. I., Pilkis, S. J., Weber, I. T. and Polonsky, K. S. (1996) Annual Review of Physiology 58, 171–86
5 Velho, G., Petersen, K. F., Perseghin, G., Hwang, J. H., Rothman, D. L., Pueyo, M. E., Cline, G. W., Froguel, P. and Shulman, G. I. (1996) Journal of CLinical Investigation 98, 1755–61
6 Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240–6
7 Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226–30
8 Caro, J. F., Triester, S., Patel, V. K., Tapscott, E. B., Frazier, N. L. and Dohm, G. L. (1995) Hormone & Metabolic Research 27, 19–22
9 Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287–95

10 Shiota, M., Postic, C., Fujimoto, Y., Jetton, T. L., Dixon, K., Pan, D., Grimsby, J., Grippo, J. F., Magnuson, M. A. and Cherrington, A. D. (2001) Diabetes 50, 622–9
11 Ferre, T., Pujol, A., Riu, E., Bosch, F. and Valera, A. (1996) Proceedings of the National Academy of Sciences of the United States of America 93, 7225–30
12 Seoane, J., Barbera, A., Telemaque-Potts, S., Newgard, C. B. and Guinovart, J. J. (1999) Journal of Biologica Chemistry 274, 31833–8
13 Moore, M. C., davis, S. N., Mann, S. L. and Cherrington, A. D. (2001) Diabetes Care 24, 1882–7
14 Alvarez, E., Roncero, I., Chowen, J. A., Vazquez, P. and Blazquez, E. (2002) Journal of Neurochemistry 80, 45–53
15 Lynch, R. M., Tompkins, L. S. Brooks, H. L., Dunn-Meynell, A. A. and Levin, B. E. (2000) Diabetes 49, 693–700
16 Roncero, I., Alvarez, E., Vazquez, P. and Blazquez, E. (2000) Journal of Neurochemistry 74, 1848–57
17 Yang, X. J., Kow, L. M., Funabashi, T. and Mobbs, C. V. (1999) Diabetes 48, 1763–1772
18 Schuit, F. C., Huypens, P., Heimberg, H. and Pipeleers, D. G. (2001) Diabetes 50, 1–11
19 Levin, B. E. (2001) International Journal of Obesity 25
20 Alvarez, E., Roncero, I., Chowen, J. A., Thorens, B. and Blazquez, E. (1996) Journal of Neurochemistry 66, 920–7
21 Mobbs, C. V., Kow, L. M. and Yang, X. J. (2001) American Journal of Physiology—Endocrinology & Metabolism 281, E649–54
22 Levin, B. E., Dunn-Meynell, A. A. and Routh, V. H. (199) American Jounal of Physiology 276, R1223–31
23 Spanswick, D., Smith, M. A., Groppi, V. E., Logan, S. D. and Ashford M. L. (1997) Nature 390, 521–5
24 Spanswick, D., Smith, M. A., Mirshamsi, S., Routh, V. H. and Ashford, M. L. (2000) Nature Neuroscience 3, 757–8
25 Levin, B. E. and Dunn-Meynell, A. A. (1997) Brain Research 776, 146–53
26 Levin, B. E., Govek, E. K. and Dunn-Meynell, A. A. (1998) Brain Research 808, 317–9
27 Levin, B. E., Brown, K. L. and Dunn-Meynell, A. A. (1996) Brain Research 739, 293–300
28 Rowe, I. C., Boden, P. R. and Ashford, M. L. (1996) Journal of Physiology 497, 365–77
29 Fujimoto, K., Sakata, T., Arase, K., Kurata, K., Okabe, Y. and Shiraishi, T. (1985) Life Sciences 37, 2475–82
30 Kurata, K., Fujimoto, K. and Sakata, T. (1989) Metabolism: Clinical & Experimental 38, 46–51
31 Kurata, K., Fujimoto, K., Sakata, T., Etou, H. and Fukagawa, K. (1986) Physiology & Behavior 37, 615–20

The invention claimed is:

1. A compound of Formula (II) or a salt, solvate, or prodrug thereof

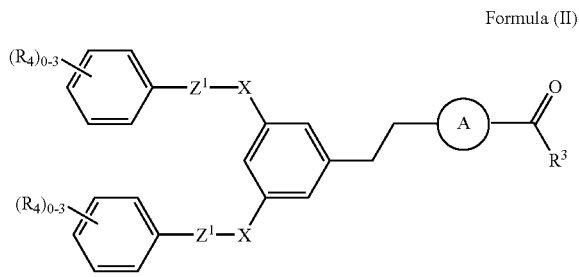

Formula (II)

wherein
A is pyridyl;
$R^3$ is selected from OH, —O-$C_{1-6}$alkyl, and $NHR^6$;
each $R^4$ is independently from halo, —$C_{3-a}F_a$, CN, $NO_2$, $NH_2$, $C_{1-6}$alkyl, —$OC_{1-6}$alkyl, —COOH, —C(O)$OC_{1-6}$ alkyl, OH, phenyl optionally substituted with $C_{1-6}$alkyl, or —C(O)$OC_{1-6}$alkyl, and $R^5$—$X^1$—;
$R^5$ is selected from hydrogen, $C_{1-6}$alkyl, —$CH_{3-a}F_a$, phenyl, naphthyl, heterocyclyl, and $C_{3-7}$cycloalkyl; wherein $R^5$ is optionally substituted with halo, $C_{1-6}$alkyl, —$CH_{3-a}F_a$, CN, $NO_2$, $NH_2$, COOH, or —C(O)$OC_{1-6}$alkyl, and wherein each phenyl, naphthyl, or heterocyclyl ring in $R^5$ is optionally substituted with halo, $CH_{3-a}F_a$, CN, $NO_2$, $NH_2$, $C_{1-6}$alkyl, —$OC_{1-6}$ alkyl, COOH, —C(O)$OC_{1-6}$alkyl, or OH;
$R^6$ is selected from hydrogen, $C_{1-6}$alkyl, $OC_{1-6}$alkyl, $SO_2C_{1-6}$alkyl, and $(CH_2)_{0-3}OH$;
each X is a linker independently selected from —O—Z—, —O—Z—O—Z—, —OC(O)—Z—, —S—Z—, —SO—Z—, —$SO_2$—Z—, —$SO_2N(R^7)$—Z—, and —$S(O)_2N(R^7)C(O)$—Z—;
each $X^1$ is a linker independently selected from —Z—, —O—Z—, —O—Z—O—Z—, —C(O)O—Z—, —OC(O)—Z—, —S—Z—, —SO—Z—, —$SO_2$—Z—, —$N(R^7)$—Z—, —$N(R^7)SO_2$—Z—, —$SO_2N(R^7)$—Z—, —$(CH_2)_{1-4}$—, —CH=CH—Z—, —C≡C—Z—, —$N(R^7)CO$—Z—, —$C(O)N(R^7)$—Z—, —$C(O)N(R^7)S(O)_2$—Z—, —$S(O)_2N(R^7)C(O)$—Z—, —C(O)—Z—, and a direct bond;
each $R^7$ is independently selected from hydrogen, $C_{1-6}$alkyl and —$C_{2-4}$alkyl-O-$C_{1-4}$alkyl;
each Z is a direct bond;
each $Z^1$ is independently selected from a direct bond, $C_{2-6}$alkenylene and a group of the formula —$(CH_2)_p$—$C(R^6)_2$—$(CH_2)_q$—;
each a is independently 1, 2 or 3;
p is 0, 1 or 2;
q is 0, 1 or 2; and
p+q<4.

2. A compound according to claim 1 or a salt, solvate, or prodrug thereof, wherein
X is independently selected from: —O—Z— or $SO_2N(R^7)$—Z—; and
$Z^1$ is independently selected from a direct bond, —$CH_2$—, —$(CH_2)_2$— and

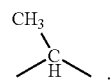

3. A pharmaceutical composition, comprising a compound according to claim 1 or 2, or a salt, solvate, or prodrug thereof, together with a pharmaceutically acceptable diluent or carrier.

4. A method of treating diabetes, comprising administering to a patient a compound of claim 1 or 2, or a salt, solvate, or prodrug thereof.

5. A method of treating obesity, comprising administering to a patient a compound of claim 1 or 2, or a salt, solvate, or prodrug thereof.

* * * * *

UNITED STATES PATENT AND TRADEMARK OFFICE
CERTIFICATE OF CORRECTION

PATENT NO.       : 7,199,140 B2                                    Page 1 of 1
APPLICATION NO.  : 10/482264
DATED            : April 3, 2007
INVENTOR(S)      : Barry Hayter et al.

It is certified that error appears in the above-identified patent and that said Letters Patent is hereby corrected as shown below:

In Claim 1, column 57, line 55, delete

" 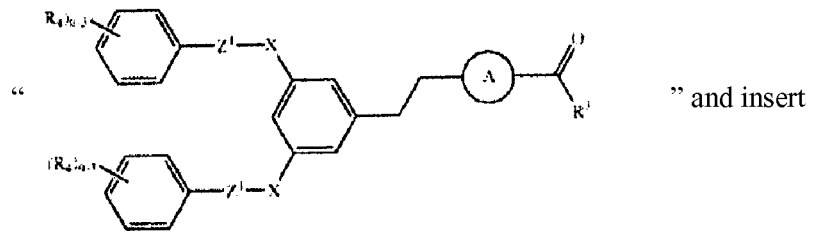 " and insert

-- 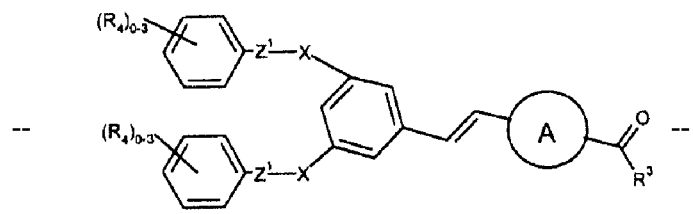 --

Signed and Sealed this

Sixteenth Day of December, 2008

JON W. DUDAS
*Director of the United States Patent and Trademark Office*